United States Patent
Dandiker

(10) Patent No.: US 11,976,065 B2
(45) Date of Patent: *May 7, 2024

(54) IMIQUIMOD COCRYSTALS

(71) Applicant: CELISTA PHARMACEUTICALS LLC, Edina, MN (US)

(72) Inventor: Yogesh Dandiker, Edina, MN (US)

(73) Assignee: CELISTA PHARM ACEUTICALS LLC, Edina, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/002,221

(22) PCT Filed: Jun. 23, 2021

(86) PCT No.: PCT/US2021/038627
§ 371 (c)(1),
(2) Date: Dec. 16, 2022

(87) PCT Pub. No.: WO2021/262814
PCT Pub. Date: Dec. 30, 2021

(65) Prior Publication Data
US 2023/0227448 A1     Jul. 20, 2023

Related U.S. Application Data

(60) Provisional application No. 63/054,019, filed on Jul. 20, 2020, provisional application No. 63/042,704, filed on Jun. 23, 2020.

(51) Int. Cl.
*C07D 471/04* (2006.01)
(52) U.S. Cl.
CPC .................... *C07D 471/04* (2013.01)

(58) Field of Classification Search
CPC ................................................... C07D 471/04
See application file for complete search history.

(56) References Cited

U.S. PATENT DOCUMENTS

| 7,927,613 | B2 | 4/2011 | Almarsson et al. |
| 8,883,838 | B2 | 11/2014 | Shanler et al. |
| 2009/0182004 | A1* | 7/2009 | Winckle ................. A61K 47/38 514/293 |

OTHER PUBLICATIONS

Guedes et al., "Imiquimod/beta-Cyclodextrin Inclusion Complex: Experimental and Theoretical Studies," Journal of Brazilian Chemistry Society 31 (8):1732-1745. (Year: 2020).*
Guedes et al., "Imiquimod/beta-Cyclodextrin Inclusion Complex: Experimental and Theoretical Studies," Journal of Brazilian Chemistry Society 31(8):1732-1745 (2020).
Karagianni et al., "Pharmaceutical Cocrystals: New Solid Phase Modification Approaches for the Formulation of APIs," Pharmaceutics 10(1)18 (2018).
Lo et al., "Ferulic acid altered IL-17A/IL-17RA interaction and protected against imiquimod-induced psoriasis-like skin injury in mice," Food and Chemical Toxicology 129:365-375 (2019).
The International Search Report and Written Opinion dated Nov. 26, 2021 in International Application No. PCT/US2021/038627.

* cited by examiner

*Primary Examiner* — Michael Barker
*Assistant Examiner* — Jed A Kucharczk
(74) *Attorney, Agent, or Firm* — MEDLER FERRO WOODHOUSE & MILLS PLLC

(57) ABSTRACT

The invention relates to novel crystalline forms of imiquimod formed with ferulic acid, acetic acid, coumaric acid, citric acid, or tartaric acid, to methods of making these cocrystals, and to compositions containing the cocrystals.

19 Claims, 15 Drawing Sheets

IMIQUIMOD COCRYSTALS

BACKGROUND OF THE INVENTION

Imiquimod is a synthetic small molecule active pharmaceutical ingredient (API). It is a toll-like receptor (TLR) agonist that induces anti-tumor activity by activating the immune system through this receptor (TLR7) which stimulates both innate and adaptive immunity. Imiquimod is currently available as a cream with indications for actinic keratosis, superficial basal cell carcinoma and external genital warts. Imiquimod in a cream formulation suffers from poor bioavailability (0.6%) leading to poor efficacy. Around 97-98% of actinic keratosis patients and 90%-100% basal cell carcinoma patients using imiquimod cream experience painful erythema of the skin due to a high amount of residual drug remaining on the skin for a minimum of 8 hours/day for several weeks due to minimal absorption of imiquimod from the cream.

Therapeutic efficacy is a primary concern for an API, but this efficacy can be affected by the pharmacological properties of the API. The salt and/or solid-state form (e.g., crystalline or amorphous forms) of a drug candidate impacts its pharmacological properties. For example, each salt or each solid form of a drug candidate can have different solid state (physical and chemical) properties. The differences in physical properties exhibited by different solid forms of an API, such as a molecular complex, cocrystal, salt, or polymorph of the original compound, can affect pharmaceutical parameters of the API. For example, storage stability, compressibility and density can be important in formulation and product manufacturing. In addition, solubility and dissolution rate, which may be important factors in determining bioavailability, may be affected. Therefore, the particular solid state form of the API can significantly impact a number of factors, including the selection of a compound as an API, the pharmaceutical dosage form, the optimization of manufacturing processes, absorption by the body, and efficacy.

Active drug molecules may be made into pharmaceutically acceptable salts for therapeutic administration to the patient. Crystalline salts of a drug may offer advantages over the free form of the compound, such as improved solubility, stability, processing improvements, and different crystalline salt forms may offer greater or lesser advantages over one another. However, crystalline salt forms are not predictable, and, in fact, are not always possible to achieve. Moreover, there is no way to predict the properties of a particular crystalline salt of a compound until it is formed. As such, finding the right conditions to obtain a particular crystalline salt form of a compound, with pharmaceutically acceptable properties is challenging.

A drug cocrystal is the crystalline form made from an active pharmaceutical ingredient (API) in combination with one or more coformer(s) in a fixed stoichiometric ratio. The interactions between API and coformer are weak interactions, and the API could be in free form format or in salt format.

By cocrystallizing an API or a salt of an API with a coformer (the other component of the cocrystal), one creates a cocrystal, a new solid state form of the API which has unique properties relative to existing solid forms of the API or its salt. For example, a cocrystal may have different dissolution and/or solubility properties than the active agent itself or its salt. Improved solubility may lead to increased concentration in solution, which may, in turn, lead to increased bioavailability of the compound. Cocrystals containing APIs can, therefore, be used to deliver APIs therapeutically. New drug formulations comprising cocrystals of APIs with pharmaceutically acceptable coformers may, in some cases, have superior properties over existing drug formulations. However, cocrystal formation is also unpredictable, and not always possible. Moreover, there is no way to predict the properties of a particular cocrystal of a compound until it is formed. As such, finding the right conditions to obtain a particular cocrystal of a compound, with pharmaceutically acceptable properties, is challenging.

SUMMARY OF THE INVENTION

In view of the disadvantages of known forms of imiquimod, one object of the present invention is to provide new crystalline forms of imiquimod, believed to be cocrystals, and to provide preparation methods, and pharmaceutical compositions thereof.

The inventors have discovered the following novel crystalline forms of imiquimod, which are believed to be cocrystals: IMQ-Fe, a ferulic acid cocrystal of imiquimod; IMQ-Ac, an acetic acid cocrystal of imiquimod; IMQ-Co, a coumaric acid cocrystal of imiquimod; IMQ-Ci, a citric acid cocrystal of imiquimod; and IMQ-Tar, a tartaric acid cocrystal of imiquimod.

Thus, the invention provides a new molecular complex of imiquimod, which is IMQ-Fe, a new molecular complex of imiquimod, which is IMQ-Ac, a new molecular complex of imiquimod, which is IMQ-Co, a new molecular complex of imiquimod, which is IMQ-Ci, and a new molecular complex of imiquimod, which is IMQ-Tar.

In another aspect, the invention provides new molecular complexes of imiquimod comprising, consisting of, or consisting essentially of IMQ-Fe, IMQ-Ac, IMQ-Co, IMQ-Ci, or IMQ-Tar.

The molecular complexes of the present invention are stable crystalline solids, and have one or more advantageous properties, such as solubility, acceptable hygroscopicity, morphology, processability and phase stability.

In another aspect, the invention relates to methods of making these cocrystals. In one embodiment, the cocrystals are made by grinding imiquimod with ferulic acid, acetic acid, coumaric acid, citric acid or tartaric acid in the presence of methanol or other suitable solvents.

The invention also relates to pharmaceutical compositions comprising a novel molecular complex of the invention and one or more pharmaceutically acceptable excipients.

In one embodiment of the invention, IMQ-Fe has the powder X-ray diffraction pattern shown in FIG. 1. In another embodiment, IMQ-Fe has a powder X-ray diffraction pattern substantially the same as that shown in FIG. 1. In another embodiment of the invention, IMQ-Fe has the DSC thermogram shown in FIG. 3. In another embodiment of the invention, IMQ-Fe has a DSC thermogram substantially the same as that shown in FIG. 3. In yet another embodiment of the invention, IMQ-Fe has the TGA curve shown in FIG. 4. In yet another embodiment of the invention, IMQ-Fe has a TGA curve substantially the same as that shown in FIG. 4. In another embodiment of the invention IMQ-Fe has the IR spectrum, over the wavelength range of 3400-600 cm$^{-1}$, shown in FIG. 8. In yet another embodiment of the invention IMQ-Fe has an IR spectrum, over the wavelength range of 3400-600 cm$^{-1}$, substantially the same as that shown in FIG. 8.

In another embodiment of the invention, the molar ratio of imiquimod to ferulic acid in IMQ-Fe is from 0.8:1.0 to 1.0:0.8. In another aspect of the invention, the ratio of imiquimod to ferulic acid in IMQ-Fe is equimolar.

In another embodiment, IMQ-Fe has a PXRD pattern using Cu-Kα radiation, expressed as 2Θ angles, with at least two peaks at positions selected from the following group: 12.3±0.2°, 13.3±0.2°, 15.1±0.2°, 17.2±0.2°, 17.7±0.2°, 17.9±0.2°, 18.7±0.2°, 19.5±0.2°, 19.9±0.2°, 23.5±0.2°, 24.7±0.2°, 25.7±0.2°, 26.9±0.2°, 27.5±0.2°, 28.1±0.2°, 28.9±0.2°, 29.5±0.2°, 30.4±0.2°, and 31.5±0.2°. In another aspect of the invention, the PXRD pattern has at least 4 peaks selected from this group. In yet another aspect, IMQ-Fe has a PXRD pattern, using Cu-Kα radiation, expressed as 2Θ angles, with peaks at positions 13.3±0.2° and 28.1±0.2°.

In one embodiment, IMQ-Fe, has an endotherm at 225-227° C.±3.0° C. as measured by DSC. In another embodiment, IMQ-Fe, has an endotherm at 226.4±3.0° C. as measured by DSC. In yet another embodiment, IMQ-Fe has an endotherm at 226.4° C., as measured by DSC.

In one aspect, IMQ-Fe is stable up to 180° C. with less than 5% weight loss as measured by TGA. In another aspect, IMQ-Fe is stable up to 180° C., with less than 4%, 3%, 2%, 1% or 0.5% weight loss as measured by TGA.

In another aspect of the invention, IMQ-Fe is anhydrous. In other aspects, IMQ-Fe may be a hydrate or solvate.

In yet another aspect, the Fourier-transform infrared spectrum of IMQ-Fe has a carboxylic acid peak at 1700.90±5.0 cm$^{-1}$. Alternatively, the peak may be at 1700.90±0.1 cm$^{-1}$, ±0.2 cm$^{-1}$, ±0.3 cm$^{-1}$, ±0.4 cm$^{-1}$, ±0.5 cm$^{-1}$, ±0.6 cm$^{-1}$, ±0.7 cm$^{-1}$, ±0.8 cm$^{-1}$, ±0.9 cm$^{-1}$, ±1.0 cm$^{-1}$, ±2.0 cm$^{-1}$, ±3.0 cm$^{-1}$ ±4.0 cm$^{-1}$, ±6.0 cm$^{-1}$, ±7.0 cm$^{-1}$, ±8.0 cm$^{-1}$, ±9.0 cm$^{-1}$, or ±10.0 cm$^{-1}$.

In one embodiment, IMQ-Fe was prepared by grinding equimolar amounts of imiquimod and ferulic acid in methanol.

The invention also relates to a method of making IMQ-Fe, comprising grinding imiquimod and ferulic acid in the presence of an organic solvent to obtain a cocrystal; wherein the cocrystal has an endotherm at about 225-227° C.±3.0° C. as measured by DSC, and/or a PXRD pattern using Cu-Kα radiation, expressed as 2Θ angles, with peaks at positions 13.3±0.2° and 28.1±0.2°. In another embodiment of this method, the molar ratio of imiquimod to ferulic acid is from 0.8:1.0 to 1.0:0.8, and the grinding is performed at 15° C.-22° C. In yet another embodiment of this method, the imiquimod and ferulic acid are present in equimolar amounts and the grinding is performed at 15° C.-22° C.

In one embodiment of the invention, IMQ-Ac has the powder X-ray diffraction pattern shown in FIG. 10. In another embodiment of the invention, IMQ-Ac has a powder X-ray diffraction pattern substantially the same as that shown in FIG. 10. In another embodiment of the invention, IMQ-Ac has the DSC thermogram shown in FIG. 11. In another embodiment of the invention, IMQ-Ac has a DSC thermogram substantially the same as that shown in FIG. 11. In yet another embodiment of the invention, IMQ-Ac has the TGA curve shown in FIG. 12. In yet another embodiment of the invention, IMQ-Ac has a TGA curve substantially the same as that shown in FIG. 12.

In one aspect of the invention, the molar ratio of imiquimod to acetic acid in IMQ-Ac is from 0.8:1.0 to 1.0:0.8. In another aspect of the invention, the ratio of imiquimod to acetic acid in IMQ-Ac is equimolar.

In yet another aspect, IMQ-Ac has a PXRD pattern using Cu-Kα radiation, expressed as 2Θ angles, with at least two peaks at positions selected from the following group: 5.9±0.2°, 6.7±0.2°, 7.9±0.2°, 9.0±0.2°, 9.8±0.2°, 12.9±0.2°, 17.1±0.2°, 20.8±0.2°, 22.7±0.2°, 25.5±0.2°, 26.1±0.2°, and 27.1±0.2°. In another aspect, the PXRD pattern has at least 4 peaks selected from this group. In another embodiment, IMQ-Ac has a PXRD pattern using Cu-Kα radiation, expressed as 2Θ angles, with peaks at positions 6.7±0.2° and 9.0±0.2°.

In yet another embodiment, IMQ-Ac has an endotherm at 72.5±3.0° C. and at 96.1±3.0° C. as measured by DSC.

In another embodiment, IMQ-Ac was prepared by grinding equimolar amounts of imiquimod and acetic acid in methanol.

The invention also relates to a method of making IMQ-Ac, comprising grinding imiquimod and acetic acid in the presence of an organic solvent to obtain a cocrystal; wherein the cocrystal has an endotherm at 72.5±3.0° C. and at 96.1±3.0° C. as measured by DSC, and/or a PXRD pattern using Cu-Kα radiation, expressed as 2Θ angles, with peaks at positions 6.7±0.2° and 9.0±0.2°. In another embodiment of this method, the molar ratio of imiquimod to acetic acid is from 0.8:1.0 to 1.0:0.8, and the grinding is performed at 15° C.-22° C. In yet another embodiment of this method, the imiquimod and acetic acid are present in equimolar amounts and the grinding is performed at 15° C.-22° C.

In one embodiment of the invention, IMQ-Co has the powder X-ray diffraction pattern shown in FIG. 13. In another embodiment, IMQ-Co has a powder X-ray diffraction pattern substantially the same as that shown in FIG. 13. In another embodiment of the invention, IMQ-Co has the DSC thermogram shown in FIG. 14. In another embodiment of the invention, IMQ-Co has a DSC thermogram substantially the same as that shown in FIG. 14. In yet another embodiment of the invention, IMQ-Co has the TGA curve shown in FIG. 15. In yet another embodiment of the invention, IMQ-Co has a TGA curve substantially the same as that shown in FIG. 15.

In one aspect of the invention, the molar ratio of imiquimod to coumaric acid in IMQ-Co is from 0.8:1.0 to 1.0:0.8. In yet another aspect, the ratio of imiquimod to coumaric acid in IMQ-Co is equimolar.

In an embodiment of the invention, IMQ-Co has a PXRD pattern, using Cu-Kα radiation, with at least two peaks at positions selected from the following group: 9.0±0.2° 2Θ, 10.2±0.2° 2Θ, 15.6±0.2° 2Θ, 16.2±0.2° 2Θ, 18.2±0.2° 2Θ, 23.2±0.2° 2Θ, 25.5±0.2° 2Θ, and 27.5±0.2° 2Θ. In another embodiment, the PXRD pattern has at least 4 peaks selected from this group. In yet another embodiment, IMQ-Co has a PXRD pattern using Cu-Kα radiation, expressed as 2Θ angles, with peaks at positions 9.0±0.2° and 25.5±0.2°.

In one aspect of the invention, IMQ-Co has an endotherm at 219.2±3.0° C. and/or at 134.1±3.0° C. as measured by DSC. In another aspect of the invention, IMQ-Co has an endotherm at 219.2±3.0° C. as measured by DSC.

In another aspect of the invention, IMQ-Co has a weight loss of 4.6%±10% at 150±2.0° C. as measured by TGA.

In yet another aspect, IMQ-Co was prepared by grinding equimolar amounts of imiquimod and coumaric acid in methanol.

The invention also relates to a method of making IMQ-Co, comprising grinding imiquimod and coumaric acid in the presence of an organic solvent to obtain a cocrystal; wherein the cocrystal has an endotherm at 219.2±3.0° C. and/or at 134.1±3.0° C. as measured by DSC, and/or has a PXRD pattern using Cu-Kα radiation, expressed as 2Θ angles, with peaks at positions 9.0±0.2° and 25.5±0.2°. In another embodiment of the method, the molar ratio of imiquimod to coumaric acid is from 0.8:1.0 to 1.0:0.8, and the grinding is performed at 15° C.-22° C. In yet another embodiment of the method, the imiquimod and coumaric acid are present in equimolar amounts and the grinding is performed at 15° C.-22° C.

In one aspect of the invention, IMQ-Ci has the powder X-ray diffraction pattern shown in FIG. 16. In another aspect of the invention, has a powder X-ray diffraction pattern substantially the same as that shown in FIG. 16. In yet another aspect of the invention, IMQ-Ci has the DSC thermogram shown in FIG. 17. In another embodiment of the invention, has a DSC thermogram substantially the same as that shown in FIG. 17. In yet another aspect of the invention, IMQ-Ci has the TGA curve shown in FIG. 18. In another embodiment of the invention, IMQ-Ci has a TGA curve substantially the same as that shown in FIG. 18.

In one embodiment of the invention, the molar ratio of imiquimod to citric acid in IMQ-Ci is from 2.2:1 to 2.0:0.8. In another embodiment, the imiquimod and citric acid in IMQ-Ci have a molar ratio of 2:1.

In yet another embodiment, has a PXRD pattern, using Cu-Kα radiation, expressed as 2Θ angles, with at least two peaks at positions selected from the following group: 5.2±0.2°, 5.8±0.2°, 7.3±0.2°, 13.1±0.2°, 13.7±0.2°, 15.2±0.2°, 21.9±0.2°, 22.7±0.2°, 23.4±0.2°, and 25.3±0.2°. In yet another embodiment, the PXRD pattern has at least 4 peaks selected from this group. In another aspect, IMQ-Ci has a PXRD pattern using Cu-Kα radiation, expressed as 2Θ angles, with peaks at positions 5.8±0.2° and 23.4±0.2°.

In one aspect, IMQ-Ci has an endotherm at 205.5±3.0° C. and/or 121.1±3.0° C. as measured by DSC.

In another aspect, IMQ-Ci has a weight loss of 5.0%±10% at 120±2.0° C. as measured by TGA.

In yet another aspect, IMQ-Ci was prepared by grinding imiquimod and citric acid in an organic solvent, wherein the imiquimod and citric acid have a molar ratio of 2:1.

The invention also relates to a method of making comprising grinding imiquimod and citric acid in the presence of an organic solvent to obtain a cocrystal; wherein the cocrystal has an endotherm at 205.5±3.0° C. and/or 121.1±3.0° C. as measured by DSC, and/or has a PXRD pattern using Cu-Kα radiation, expressed as 2Θ angles, with peaks at positions 5.8±0.2° and 23.4±0.2°. In another embodiment of the method, the molar ratio of imiquimod to citric acid is from 2.2:1 to 2.0:0.8, and the grinding is performed at 15° C.-22° C. In yet another embodiment of the method, the imiquimod and citric acid have a molar ratio of 2:1, and the grinding is performed at 15° C.-22° C.

In one embodiment of the invention, IMQ-Tar has the powder X-ray diffraction pattern shown in FIG. 19. In another embodiment of the invention, IMQ-Tar has a powder X-ray diffraction pattern substantially the same as that shown in FIG. 19. In another embodiment of the invention, IMQ-Tar has the TGA curve shown in FIG. 20. In yet another embodiment of the invention, IMQ-Tar has a TGA curve substantially similar to that shown in FIG. 20.

In one aspect of the invention, the molar ratio of imiquimod to tartaric acid in IMQ-Tar is from 2.2:1 to 2.0:0.8. In yet another aspect of the invention, the imiquimod and tartaric acid in IMQ-Tar have a molar ratio of 2:1.

In yet another aspect, IMQ-Tar has a PXRD pattern using Cu-Kα radiation, expressed as 2Θ angles, with at least two peaks at positions selected from the following group: 6.6±0.2°, 8.5±0.2°, 13.3±0.2°, 14.7±0.2°, 17.8±0.2°, 19.0±0.2°, 20.9±0.2°, 22.4±0.2°, 26.1±0.2°, 27.5±0.2°, and 29.8±0.2°. In another aspect, the PXRD pattern has at least 4 peaks selected from this group. In yet another aspect, IMQ-Tar has a PXRD pattern using Cu-Kα radiation, expressed as 2Θ angles, with peaks at positions 8.5±0.2° and 26.1±0.2°.

In another embodiment of the invention, IMQ-Tar does not melt below 200° C. as measured by DSC.

In another embodiment of the invention, IMQ-Tar has a weight loss of 5.2%±10% at 170±2.0° C. as measured by TGA.

In yet another embodiment, IMQ-Tar was prepared by grinding imiquimod and tartaric acid in methanol, wherein the imiquimod and tartaric acid have a molar ratio of 2:1.

The invention also relates to a method of making IMQ-Tar, comprising grinding imiquimod and tartaric acid in the presence of an organic solvent to obtain a cocrystal, wherein the cocrystal does not melt below 200° C. as measured by DSC, and/or has a PXRD pattern using Cu-Kα radiation, expressed as 2Θ angles, with peaks at positions 8.5±0.2° and 26.1±0.2°. In another aspect of the method, the molar ratio of imiquimod to tartaric acid is from 2.2:1 to 2.0:0.8, and the grinding is performed at 15° C.-22° C. In yet another aspect of the method, the imiquimod and citric acid have a molar ratio of 2:1 and the grinding is performed at 15° C.-22° C.

The invention also relates to a composition comprising one or more of any of IMQ-Fe, IMQ-Ac, IMQ-Co, IMQ-Ci or IMQ-Tar, and one or more pharmaceutically acceptable excipients.

The cocrystals of the invention have one or more advantageous properties, compared to known forms of imiquimod, such as better bioavailability, higher solubility, and improved hygroscopicity, morphology, processability, flowability, and/or stability (such as relative humidity stress, thermal stress, chemical stability and solution stability). The crystalline forms of the present invention are more suitable than known forms of imiquimod for use as the active ingredient in pharmaceutical formulations. For example, the known form of imiquimod has low water solubility and very low topical bioavailability. The crystalline forms of the present invention have higher solubility, good skin permeation properties and increased bioavailability. They also have good phase stability which can better ensure the quality, safety and stability of the active ingredients and formulations containing them.

DETAILED DESCRIPTION OF THE INVENTION

Figure 1:
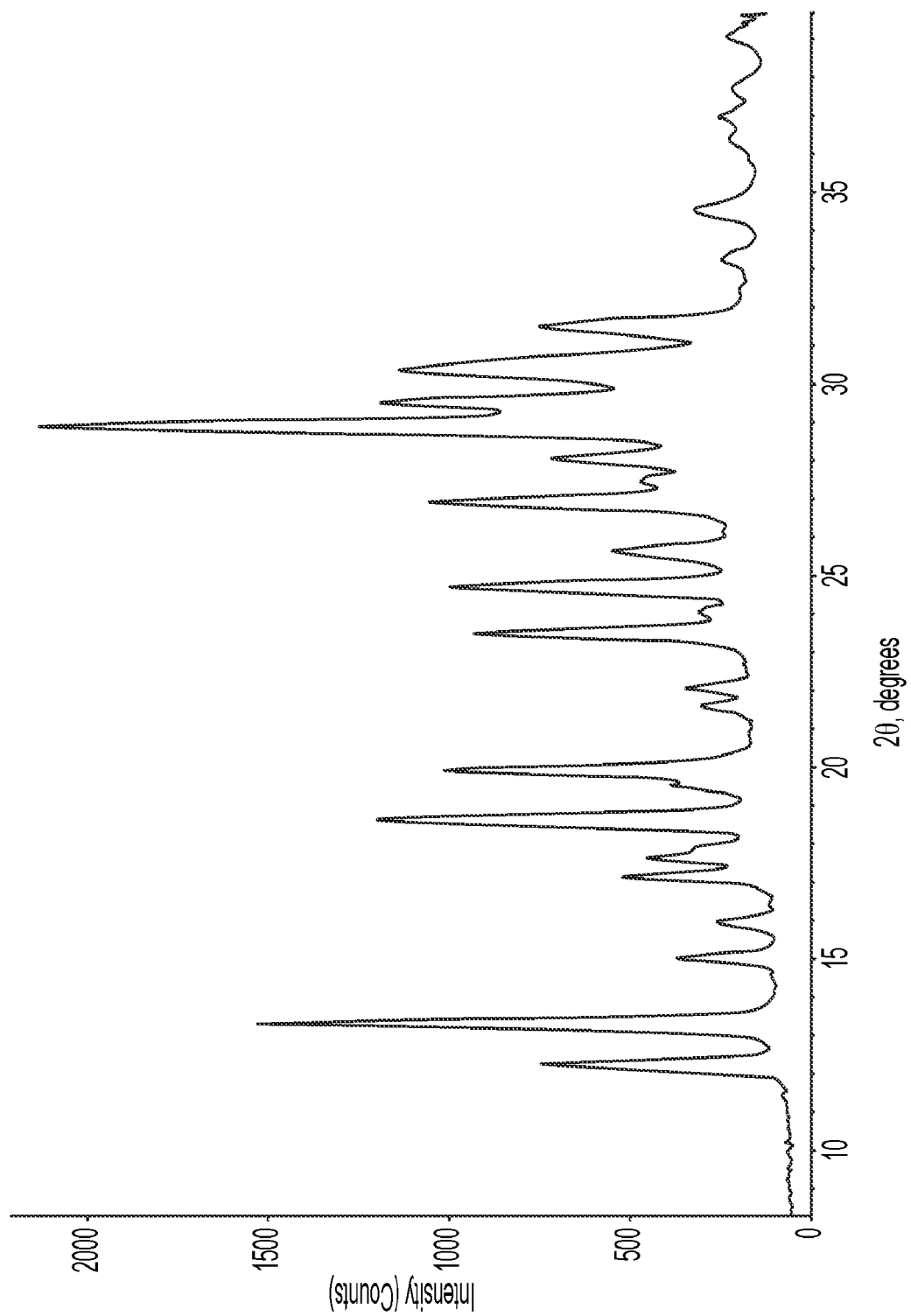
FIG. 1 is the PXRD pattern of the imiquimod-ferulic acid cocrystal IMQ-Fe.

It is believed that the novel crystalline forms of imiquimod described herein are cocrystals. Thus, the invention relates to the following novel cocrystals of imiquimod: IMQ-Fe, a ferulic acid cocrystal of imiquimod; IMQ-Ac, an acetic acid cocrystal of imiquimod; IMQ-Co, a coumaric acid cocrystal of imiquimod; IMQ-Ci, a citric acid cocrystal of imiquimod; and IMQ-Tar, a tartaric acid cocrystal of imiquimod.

A cocrystal is a crystalline material made from two or more components (e.g., an active pharmaceutical ingredient (API) in combination with a coformer) in a fixed stoichiometric ratio. A cocrystal can be a multi-component crystal, such as a binary cocrystal formed between two neutral solids or a pluralistic cocrystal.

Unlike salts, where the components of the crystal lattice are in an ionized state, the cocrystals' components are in a neutral state and interact through non-ionic interactions. Hence, one difference between salts and cocrystals is that in salt formation there is a proton transfer and ionization, while this does not occur in a cocrystal. Rather, the interactions between API and coformer in a cocrystal are not ionic bond interactions nor covalent bond interactions. They are weak interactions such as hydrogen bonds, van der Waals forces, $\pi$-$\pi$ interactions or halogen bonds.

Cocrystals can exist as polymorphs, or as hydrates or solvates.

A crystalline form of a compound, a crystalline salt of the compound, or a cocrystal containing the compound or its salt form generally possesses distinct crystallographic, thermal and spectroscopic properties when compared to other crystalline forms having the same chemical composition.

Crystallographic and spectroscopic properties of a particular form may be measured by PXRD, or single crystal X-ray crystallography, among other techniques.

Fourier-transform IR spectroscopy (FTIR), which can be used for the simultaneous study of the spectra of the cocrystals' individual components and of their final mixture with polymer matrices, etc., is an important tool in detecting cocrystal formation and in the elucidation of their structures. The cocrystal provides a different spectrum from that of the components' mixture due to the presence of hydrogen bonds, especially when carboxylic acid is used as a coformer and when a neutral hydrogen bond O—H _ _ _ N is formed between an acid and a base. Clear IR spectra differences are observed between a neutral carboxylic acid functional group and a carboxylic anion. Neutral carboxylate (—COOH) shows a strong tension band of C=O at about 1700 cm).

A particular crystalline form of a compound, its salt, or a cocrystal of the compound, also often exhibit distinct thermal behavior. Thermal behavior can be measured in the laboratory by techniques such as capillary melting point, TGA, or DSC. The thermal behavior of an API, such as its melting point, can impact formulation of the API. The melting point of the solid form of a drug is optionally high enough to avoid melting or plastic deformation during standard processing operations, as well as concretion of the drug by plastic deformation on storage. For some formulation processing methods, higher melting points may be desirable, e.g., above about 100° C.

Specifically, and further without wishing to be bound, it is believed that the novel cocrystals of imiquimod that have been discovered are an anhydrous ferulic acid cocrystal of imiquimod having approximately one mole of imiquimod and approximately one mole of ferulic acid; an acetic acid cocrystal of imiquimod having approximately one mole of imiquimod and approximately one mole of acetic acid; a coumaric acid cocrystal of imiquimod having approximately one mole of imiquimod and approximately one mole of coumaric acid; a citric acid cocrystal of imiquimod having approximately two moles of imiquimod and approximately one mole of citric acid; and a tartaric acid cocrystal of imiquimod having approximately two moles of imiquimod and approximately one mole of tartaric acid.

The molar ratio of imiquimod to coformer for IMQ-Fe, IMQ-Ac, IMQ-Co may alternatively be from 0.7:1.0 to 1.0:0.7, 0.8:1.0 to 1.0:0.8, 0.9:1.0 to 1.0:0.9. For example, the molar ratio of imiquimod to coformer (Fe, Ac or Co), may be 0.7:1.0, 0.75:1.0, 0.8:1.0, 0.85:1.0, 0.9:1.0, 0.95:1.0, 0.98:1.0, 0.99:1.0, 1.0:1.0, 1.0:0.99, 1.0:0.98, 1.0:0.95, 1.0:0.90, 1.0:0.85, 1.0:0.8, 1.0:0.75, or 1.0:0.7. The molar ratio of imiquimod to coformer for IMQ-Ci and IMQ-Tar may alternatively be from 2.3:1 to 2.0:0.7, 2.2:1 to 2.0:0.8, or 2.1:1 to 2.0:0.7. For example, the molar ratio of imiquimod to coformer (Ci or Tar), may be 2.3:1.0, 1.25:1.0, 2.2:1.0, 2.15:1.0, 2.1:1.0, 2.0:1.0, 2.0:0.99, 2.0:0.98, 2.0:0.95, 2.0:0.90, 2.0:0.85, 2.0:0.8, 2.0:0.75, or 2.0:0.7.

In another aspect, the invention relates to methods of making these cocrystals. Effective cocrystal preparation methods in use today can be classified as: (1) solid (neat grinding, solvent-assisted grinding, sonication); or (2) solvent-based (slurring, solvent evaporation, crystallization from solution or active cocrystallization and antisolvent addition). [Karagianni, A. et al., "Pharmaceutical Cocrystals: New Solid Phase Modification Approaches for the Formulation of APIs," *Pharmaceutics,* 10, 18, 2018; Qiao, N et al., "Pharmaceutical cocrystals: An overview", International Journal of Pharmaceutics, 419, 2011. 1-11.].

The most common method for industrial (large scale) production of cocrystals is the cocrystallization of an API by a supersaturated solution in the presence of a coformer. In most cases, about 40% supersaturation is achieved through the slow cooling of an undersaturated mixture until the dissolution limit is reached. Additionally, solution mediated phase transitions can be induced by manipulating the amount of the coformer (reaction cocrystallization).

In one embodiment, the cocrystals of the invention may be made by solid state grinding a molar ratio of imiquimod with ferulic acid, acetic acid, coumaric acid, citric acid, or tartaric acid in the presence of methanol or another suitable solvent, as described below. The solvent may be, e.g., methanol, acetone, ethanol, acetonitrile, or another organic solvent. The amount of solvent added is about 100 μL-1.0 mL per 1.0 g of total material (imiquimod+coformer). For lab scale batches imiquimod, coformer and solvent are mixed for about 15 to about 45 minutes. For 1 gram of material, mixing will be done for about 30-45 minutes. For larger scale production, the mixing period may need to be increased. If the material is ground for about 30 minutes, a small amount of methanol should be added at regular intervals, such as about every 10 minutes. Batches are made at room temperature, 15-22° C., preferably 18-22° C. The temperature may be about, e.g., 15, 16, 17, 18, 19, 20, 21 or 22° C. or a temperature between these values. The solids (imiquimod and coformer) will partially dissolve during grinding, such that they form a wet powder or paste. During grinding most of the solvent will evaporate. The mixture can be dried in a vacuum oven at room temperature, if needed.

In the method provided by the invention, the molar ratio of imiquimod to coformer for IMQ-Fe, IMQ-Ac, and IMQ-Co may be from 0.7:1.0 to 1.0:0.7, 0.8:1.0 to 1.0:0.8, 0.9:1.0 to 1.0:0.9. For example, the molar ratio of imiquimod to coformer (Fe, Ac or Co), may be 0.7:1.0, 0.75:1.0, 0.8:1.0, 0.85:1.0, 0.9:1.0, 0.95:1.0, 0.98:1.0, 0.99:1.0, 1.0:1.0, 1.0:0.99, 1.0:0.98, 1.0:0.95, 1.0:0.90, 1.0:0.85, 1.0:0.8, 1.0:0.75, or 1.0:0.7. In a preferred embodiment of the method, the molar ratio of imiquimod to coformer for IMQ-Fe, IMQ-Ac, and IMQ-Co is 1:1 imiquimod to coformer. The molar ratio of imiquimod to coformer for IMQ-Ci and IMQ-Tar may be from 2.3:1 to 2.0:0.7, 2.2:1 to 2.0:0.8, or 2.1:1 to 2.0:0.9. For example, the molar ratio of imiquimod to coformer (Ci or Tar), may be 2.3:1.0, 1.25:1.0, 2.2:1.0, 2.15:1.0, 2.1:1.0, 2.0:1.0, 2.0:0.99, 2.0:0.98, 2.0:0.95, 2.0:0.90, 2.0:0.85, 2.0:0.8, 2.0:0.75, or 2.0:0.7. In a preferred embodiment of the method, the molar ratio of imiquimod to coformer for IMQ-Ci and IMQ-Tar is 2:1 imiquimod to coformer.

The cocrystals of the present invention can formulated as pharmaceutical dosage forms. Thus, the invention also relates to pharmaceutical compositions containing the novel cocrystals and one or more pharmaceutically acceptable excipients. Depending on the type of pharmaceutical composition, the pharmaceutically acceptable excipient may be chosen from any one or a combination of excipients known in the art. The choice of the pharmaceutically acceptable excipient depends upon the pharmaceutical form and the desired method of administration to be used. Remington: The Science and Practice of Pharmacy. 22$^{nd}$ ed. London, UK: Pharmaceutical Press; 2012, discloses various excipients used in formulating pharmaceutical compositions and techniques for the preparing pharmaceutical compositions.

Definitions

As used herein, the following words and phrases are generally intended to have the meanings as set forth below, except to the extent that the context in which they are used indicates otherwise.

The terms "imiquimod" and "IMQ" refer to the compound with the chemical designation 1-(2-methylpropyl)-1H-imidazo[4,5-c]quinolin-4-amine. Imiquimod has a molecular formula of $C_{14}H_{16}N_4$ and a molecular weight of 240.3. It has the following structure:

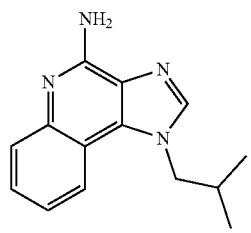 [SMILES: CC(C)Cn1cnc2c(N)nc3ccccc3c21]

As used herein, the term "molecular complex" is used to mean a complex is a molecular entity formed by loose association involving two or more component molecular entities (ionic or uncharged) and encompasses cocrystals.

As used herein, the terms IMQ-Fe, ferulic acid cocrystal of imiquimod, imiquimod-ferulic acid cocrystal, and variations thereof, are used interchangeably to refer to the novel molecular complex formed from imiquimod and ferulic acid, believed to be a cocrystal, described herein. An alternative name for IMQ-Fe is IMQ-FA.

As used herein, the terms IMQ-Ac, acetic acid cocrystal of imiquimod, imiquimod-acetic acid cocrystal, and variations thereof, are used interchangeably to refer to the novel molecular complex formed from imiquimod and acetic acid, believed to be a cocrystal, described herein.

As used herein, the terms IMQ-Co, coumaric acid cocrystal of imiquimod, imiquimod-coumaric acid cocrystal, and variations thereof, are used interchangeably to refer to the novel molecular complex formed from imiquimod and coumaric acid, believed to be a cocrystal, described herein.

As used herein, the terms citric acid cocrystal of imiquimod, imiquimod-citric acid cocrystal, and variations thereof, are used interchangeably to refer to the novel molecular complex formed from imiquimod and citric acid, believed to be a cocrystal, described herein.

As used herein, the terms IMQ-Tar, tartaric acid cocrystal of imiquimod, imiquimod-tartaric acid cocrystal, and variations thereof, are used interchangeably to refer to the novel molecular complex, formed from imiquimod and tartaric acid, believed to be a cocrystal, described herein.

As used herein, "mole ratio" is the ratio of moles of one substance to the moles of another substance in a balanced equation.

As used herein, the term "PXRD" refers to powder x-ray diffraction. The PXRD data disclosed herein were obtained using a D8 ADVANCE; Bruker AXS, Madison, WI, USA powder diffractometer. Powder samples of 1 g were exposed to Cu-Kα radiation (40 kV and 40 mA) over an angular range of 5-40° 2θ with a step size of 0.0196° and a dwell time of 0.5 s. Data analysis was performed using commercially available software (JADE Materials Data, Inc., Livermore, CA).

As used herein, the term "DSC" refers to differential scanning calorimetry. DSC data disclosed herein were obtained using a model Q2000, TA Instruments, differential scanning calorimeter equipped with a refrigerated cooling accessory. A 10 mg sample was hermetically sealed in an aluminum pan. All measurements were performed at a heating rate of 10° C./min under nitrogen purge (50 mL/min). The instrument was calibrated with indium.

As used herein, the term "TGA" refers to thermogravimetric analysis. TGA data disclosed herein were obtained using a TA Instruments, New Castle, DE, model Q50 TGA, thermogravimetric analyzer. A 10 mg sample was placed in an aluminum sample pan and heated from RT to up the melting point of the cocrystal at 10° C./min under dry nitrogen purge (50 mL/min). The TGA data were analyzed using commercial software (Universal Analysis 2000, TA Instruments, New Castle, DE). Nickel and Alumel™ were used as the calibration standards.

The melting points and endotherms recited in the embodiments of the invention may vary by ±0.1° C., ±0.2° C., ±0.3° C., ±0.4° C., ±0.5° C., ±0.6° C., ±0.7° C., ±0.8° C., ±0.9° C., ±1.0° C., ±2.0° C., ±3.0° C., ±4.0° C., ±5.0° C., ±6.0° C., ±7.0° C., ±8.0° C., ±9.0° C., or ±10.0° C.

As used herein, the term "IR" refers to infrared, and "FTIR" refers to Fourier-transform IR spectroscopy. The FTIR spectroscopy data disclosed herein was obtained using a Vertex 70, Bruker, Ettlingen, Germany, spectrometer, equipped with a globar mid-IR source), using an attenuated total reflectance (ATR) accessory (single reflection germanium crystal) and a DLaTGS detector. The resolution was 4 cm$^{-1}$, and 64 scans were acquired in the range of 4000-400 cm$^{-1}$. The peak positions were determined using OPUS software peak picking function.

As used herein with respect to the various analytical techniques described herein and data generated therefrom, the term "substantially the same as" is meant to convey that a particular set of analytical data is, within acceptable scientific limits, sufficiently similar to that disclosed herein such that one of skill in the art would appreciate that the form of the molecular complex is the same as that of the present invention.

One of skill in the art would appreciate that certain analytical techniques, such as, for example, PXRD, TGA, DSC, IR spectroscopy, will not produce exactly the same results every time due to, for example, instrumental variation, sample preparation, operator variability, etc. By way of example only, PXRD results (i.e. peak locations, intensities, and/or presence) may vary slightly from sample to sample, despite the fact that the samples are, within accepted scientific principles, the same form, and this may be due to, for example, preferred orientation, varying degree of crystallinity, or varying solvent or water content. It is well within the ability of those skilled in the art, looking at the data as a whole, to appreciate whether such differences indicate a different form, and thus determine whether analytical data being compared to those disclosed herein are substantially the same as or similar.

In this regard, and as is commonly practiced within the scientific community, it is not intended that the exemplary analytical data of the novel cocrystal forms of imiquimod disclosed herein be met literally in order to determine whether comparative data represent the same form as that disclosed and claimed herein, such as, for example, whether each and every peak of the exemplary PXRD pattern disclosed herein is present in the comparative data, in the same location, and/or of the same intensity. Rather, as discussed above, it is intended that those of skill in the art, using accepted scientific principles, will make a determination based on the data as a whole regarding whether comparative analytical data represent the same or a different form of the novel imiquimod cocrystals disclosed herein.

Further, it should be noted that varying degrees of crystallinity of a cocrystal of a compound, such as the novel cocrystals disclosed herein, may be achieved. The degree of crystallinity achieved may, for example, depend on the conditions under which a sample is prepared. Accordingly, one of skill in the art will appreciate that a particular set of analytical data may reflect a greater or lesser degree of crystallinity than the exemplary analytical data shown in the Figures herein, but appreciate that the form of the molecular complex is the same as that disclosed and claimed herein.

The "crystalline form" in the present invention is confirmed by the powder X-ray diffraction pattern, having a unique ordered molecular arrangement or configuration within the crystal lattice. It is known to those of skill in the art that experimental errors of X-ray diffraction depend on instrument conditions, sample preparation and sample purity. The 2Θ angle of the peaks of a powder X-ray diffraction pattern usually varies slightly due to the difference in the instrument and sample. The differences in peak position may vary by 1°, 0.8°, 0.5°, 0.3°, 0.2° or 0.1° 2Θ, depending on different instruments and samples, and usually ±0.2° in differences are allowed. The relative intensities of peaks may change with the change of samples, sample preparation and other experimental conditions; therefore, the order of peak intensities should not be regarded as the only or the determining factor. Due to the effect of experimental factors including sample height, peak position may shift; generally, a small amount of peak shifting is acceptable experimental error. Hence, it is easily understood for those skilled in the field that any crystalline forms having the same or similar powder X-ray diffraction pattern as that of the crystalline form of corresponding forms in the present invention should be within the scope of the present invention.

"Pure crystalline form" as used herein refers to a pure crystalline form confirmed by powder X-ray diffraction.

In some embodiments, the cocrystals of imiquimod of the present invention may be substantially pure and substantially free of other crystalline or amorphous forms of imiquimod, or other impurities. By "substantially pure", it is meant that the new crystalline form comprises at least 95% by weight of the particular cocrystal. In other embodiments, the crystalline form comprises at least 80% by weight of the particular cocrystal, at least 85% by weight, more preferably at least 90% by weight, especially at least 98% by weight, in particular at least 99% by weight.

The term "substantially all" as used herein with regard to other aspects of the present invention refers to most of the total amount, e.g., at least 80%, at least 85%, at least 90%, at least 95% or at least 99% of a total amount.

It should be noted that the novel solid forms of imiquimod disclosed herein are in crystalline form, as shown in the Figures and as discussed below. Without wishing to be bound, however, Applicants refer herein to the novel crystalline solid forms as "cocrystals," but note that the type of interaction between components in these novel crystalline solid forms may differ without consequence to either the novelty of the crystalline solid forms, or the data that is disclosed for, and relevant to, each of the crystalline solid forms, disclosed herein.

"Percent" or "%" as used herein refers to weight (w/w) percentage unless otherwise specified.

As used in the specification and the appended claims, the singular forms "a," "an," and "the" include singular and plural unless the context dictates otherwise. Thus, "a", "an" or "the", means one or more, unless specified otherwise.

The term "about" as used herein means approximately ±5% of the value. When the term "about" is used in conjunction with a numerical value or range, it modifies that value or range by extending the boundaries above and below the numerical values set forth. In general, the term "about" is used herein to modify a numerical value above and below the stated value by a variance of 10 percent of the value, up or down (higher or lower), i.e., ±10%, unless a different variance is indicated (e.g., ±30%, ±20%, ±5%, ±1%, ±0.5% etc.). The term "±10%" with regard to weight loss means a variance of 10% of the stated value is encompassed. For example, "a weight loss of 4.6%±10%" at a given temperature, as measured by TGA, means that the weight loss is 4.6%±0.46, i.e., 4.14-5.06%.

As used herein, "and/or" refers to and encompasses each of the listed items individually, as well as any and all possible combinations of one or more of the listed items.

When the terms "in" or "into" are used in the specification or the claims, it is intended to additionally mean "on" or "onto."

The terms "comprising," "consisting of" and "consisting essentially of" have their usual accepted meanings in accordance with patent law. When the term "includes" or "including" is used in the specification or the claims, it is intended to be inclusive in a manner similar to the term "comprising" as that term is interpreted when employed as a transitional word in a claim.

As used herein, the terms "optional" and "optionally" mean that the subsequently described circumstance may or may not occur, so that the description includes instances where the circumstance occurs and instances where it does not.

Where features or aspects of the disclosure or claims are described in terms of Markush groups, those skilled in the art will recognize that the disclosure is also thereby described in terms of any individual member or subgroup of members of the Markush group.

In addition, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, and the like. As a non-limiting example, each range discussed herein can be readily broken down into a lower third, middle third and upper third, and the like. As will also be understood by one skilled in the art all language such as "up to," "at least," "greater than," "less than," include the number recited and refer to ranges which can be subsequently broken down into sub-ranges as discussed above. Finally, as will be understood by one skilled in the art, a range includes each individual member. For example, a group having 1-3 members refers to groups having 1, 2, or 3 members. Similarly, a group having 1-5 members refers to groups having 1, 2, 3, 4, or 5 members, and so forth.

EXAMPLES

The disclosure is further illustrated by the following examples which are provided merely to be exemplary and do not limit the scope of the invention. Certain modifications and equivalents will be apparent to those skilled in the art and are intended to be included within the scope of the disclosure. The present disclosure provides, but is not limited to, the following formulation examples.

Example 1 (IMQ-Fe)

IMQ-Fe was prepared by weighing equimolar amounts of imiquimod and ferulic acid (40 mg imiquimod and 32 mg ferulic acid), and then mixing and mechanically grinding them with mortar and pestle for about 30 minutes at room temperature, 19-22° C. Small quantities of methanol were added at regular intervals of time. The total amount of methanol added was 20 ml. The solids (imiquimod and coformer) partially dissolved during grinding, such that they formed a wet powder or paste. During grinding most of the methanol evaporated. The mixture was dried in a vacuum oven at room temperature.

Example 2

Samples of the imiquimod-ferulic acid complex prepared above were evaluated using powder X-ray diffraction (PXRD), thermogravimetric analysis (TGA), and differential scanning calorimetry (DSC).

PXRD is a non-destructive technique widely applied in cocrystal characterization, in which the appearance or disappearance of new peaks in the PXRD patterns, compared to individual components, confirms a change in the crystalline phase and indicates the potential formation of a cocrystal.

A cocrystal should exhibit unique diffraction peaks compared to the individual components of the cocrystal. Unique diffraction peaks indicate a change in the crystalline phase and the formation of a cocrystal. The cocrystal may present lower peak intensity than the individual components, indicating a less crystalline material. This can be corroborated with DSC. Such a result could also relate to a reduction in particle size.

PXRD was performed on a 1 g sample of the imiquimod-ferulic acid complex. The powder samples were exposed to Cu-Kα radiation (40 kV and 40 mA) using a diffractometer (D8 ADVANCE; Bruker AXS, Madison, WI, USA) over an angular range of 5-40° 2θ with a step size of 0.0196° and a dwell time of 0.5 s. Data analysis was performed using commercially available software (JADE Materials Data, Inc., Livermore, CA).

The PXRD pattern of a complex prepared according to Example 1 is shown in FIG. 1. The pattern shows characteristic peaks with 2θ values at: 12.3, 13.3, 15.1, 17.2, 17.7, 17.9, 18.7, 19.5, 19.9, 23.5, 24.7, 25.7, 26.9, 27.5, 28.1, 28.9, 29.5, 30.4 and 31.5°. This PXRD pattern has characteristic peaks that appear only in the sample prepared with imiquimod and ferulic acid, and are not found in the PXRD patterns for imiquimod or ferulic acid. Crystalline imiquimod has characteristic peaks with 2θ values of 11, 15, 19, 22 and 24°. [Reference: patent CA2551616A1]. Crystalline ferulic acid has characteristic peaks with 2θ values of 9, 10, 13, 16, 18, 22, 24, 26, 29, and 32° [Reference: Rezaei et al., Improving the solubility and in vitro cytotoxicity (anticancer activity) of ferulic acid by loading it into cyclodextrin nanosponges, 2019]. The appearance and disappearance of new peaks in the PXRD pattern in the imiquimod-ferulic acid complex, compared to the patterns of the individual components (imiquimod and ferulic acid), confirms a change in the crystalline structure and indicates the formation of a new cocrystal.

Figure 2:
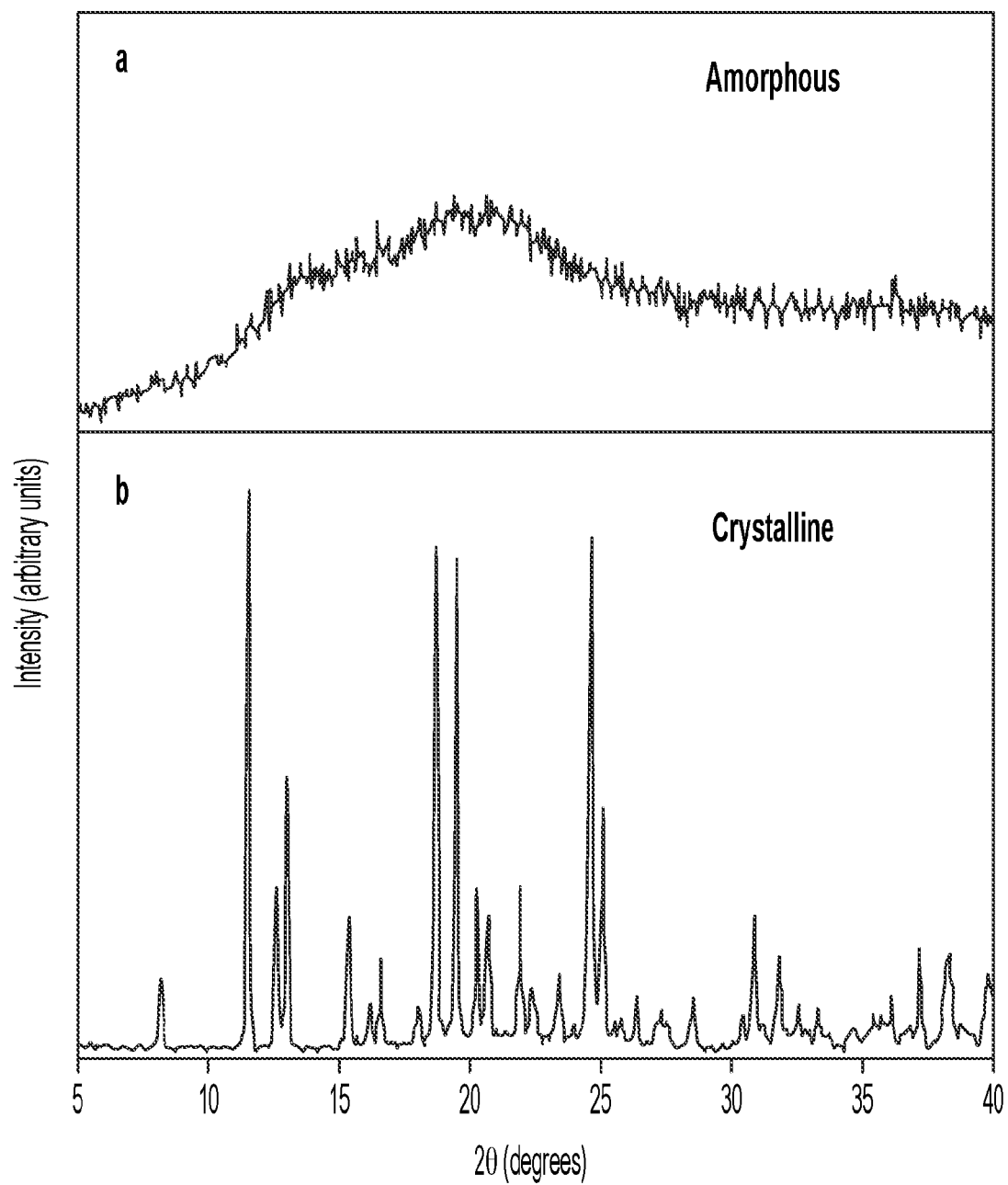
FIG. 2 is a comparison of the PXRD pattern of an amorphous substance to the PXRD pattern of the crystalline substance.

Moreover, the PXRD pattern in FIG. 1 demonstrates that the sample was crystalline. FIG. 2 is a comparison of the PXRD pattern of an amorphous substance ((a) top section) to the PXRD pattern of the crystalline substance ((b) in bottom section). The amorphous material has a diffuse X-ray diffraction pattern, rather than having clear high intensity peaks found in the pattern for the crystalline material. The PXRD pattern in FIG. 1 does not have a diffuse X-ray diffraction pattern.

Cocrystals exhibit different physicochemical properties from their individual components. This includes differences between the melting point of the cocrystal and melting points of the individual components of the cocrystal. DSC is a precise technique that can be employed to evaluate the thermal behavior of cocrystals. In most cases, a single melting point is formed at an intermediate temperature compared to the melting points of the individual components.

DSC was used to evaluate the thermal behavior of a sample of the material prepared according to Example 1

(imiquimod and ferulic acid). A differential scanning calorimeter (model Q2000, TA Instruments) equipped with a refrigerated cooling accessory was used to analyze a sample. A 10 mg of sample was hermetically sealed in an aluminum pan. All measurements were performed at a heating rate of 10° C./min under nitrogen purge (50 mL/min). The instrument was calibrated with indium.

Figure 3:
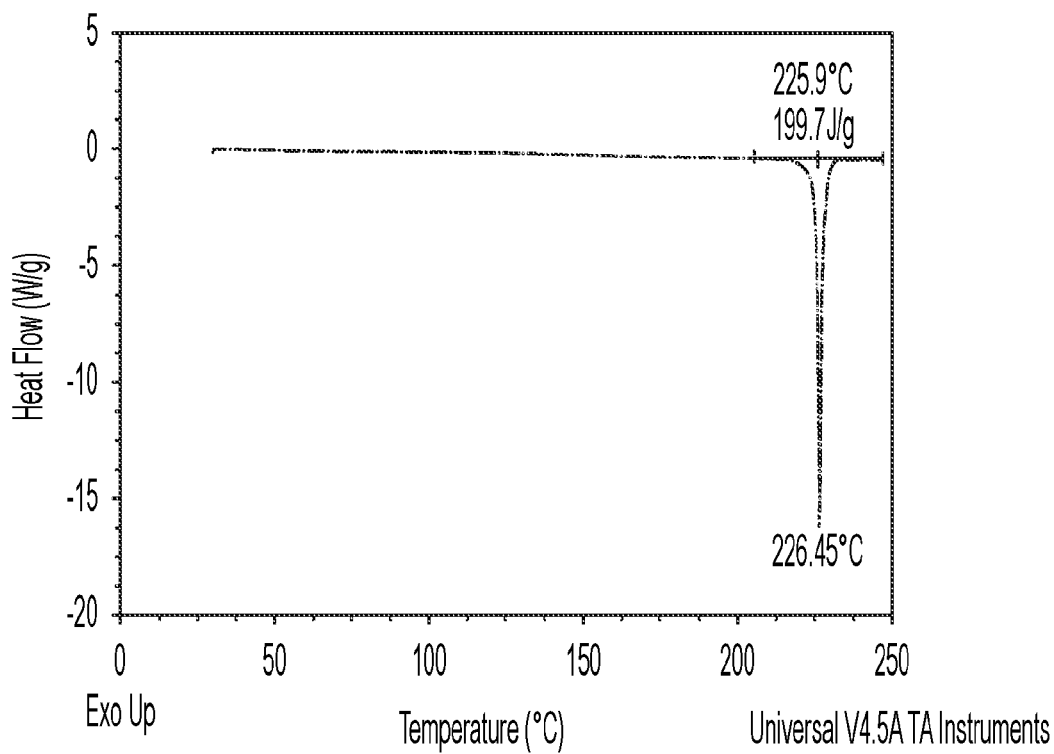
FIG. 3 is the DSC thermogram of the imiquimod-ferulic acid cocrystal IMQ-Fe.

The DSC thermogram is shown in FIG. 3. The complex has a single endotherm at about 225.9-226.45° C. This temperature falls between the melting point of imiquimod, which has a melting point of 292-296° C., and the melting point of ferulic acid, which has a melting point of 168-172° C. (form I ferulic acid Tm=175° C.). This is strong evidence that a cocrystal is formed.

TGA can be used to identify the presence of solvents in a raw material. TGA can also be used to evaluate the thermal stability of a raw material such as a cocrystal. If the material is a hydrate, there will be about 5% water loss up to 98° C. and potential degradation may also occur indicating instability under thermal conditions. If the material is anhydrous, it will be more thermally stable, because it will present a higher melting point and degradation temperature.

TGA was used to evaluate the thermal stability of the imiquimod-ferulic acid complex. In a thermogravimetric analyzer (model Q50 TGA, TA Instruments, New Castle, DE), 10 mg of sample was heated in an aluminum pan from RT to up the melting point of the cocrystal at 10° C./min under dry nitrogen purge (50 mL/min). The TGA data were analyzed using commercial software (Universal Analysis 2000, TA Instruments, New Castle, DE).

Figure 4:
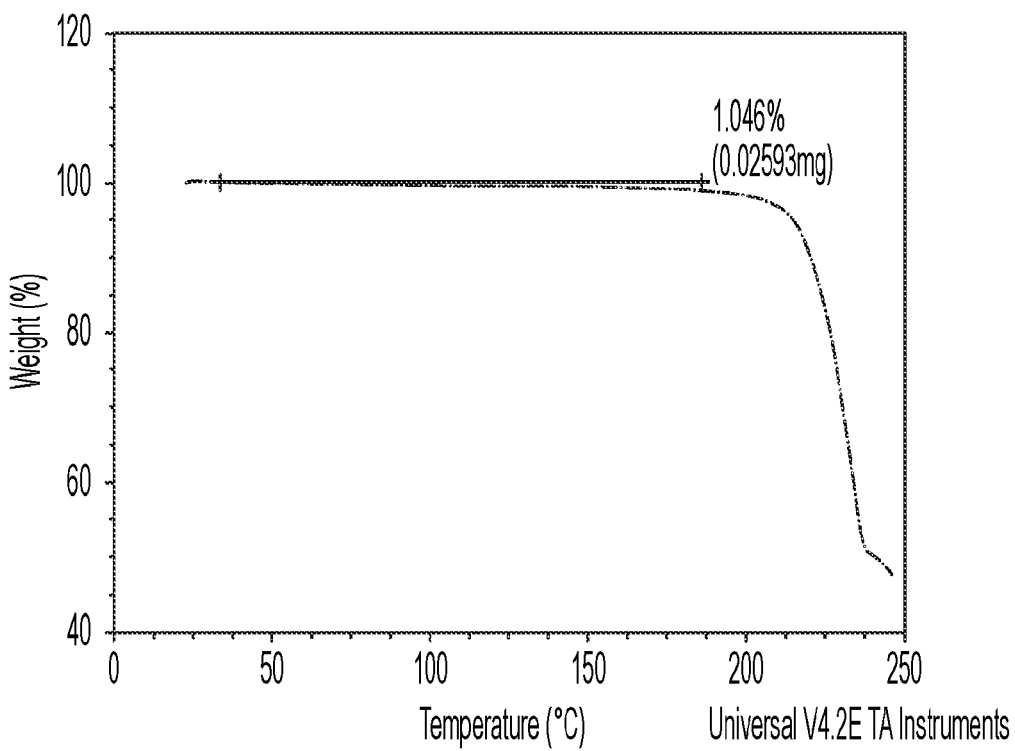
FIG. 4 is the TGA curve of the imiquimod-ferulic acid cocrystal IMQ-Fe.

As shown in FIG. 4, a single endotherm around the cocrystal melting point appeared. The curve also indicates that the cocrystal is stable up to 180° C. with negligible weight loss, which indicates that this cocrystal is anhydrous. If it were a monohydrate it would have had a water loss around 98° C. and potential degradation loss after that point.

The data generated by PXRD, DSC and TGA confirms that the newly formed imiquimod-ferulic acid complex is a cocrystal. We have designated this new molecular complex IMQ-Fe.

Example 3

FTIR spectroscopy was used to confirm cocrystal formation of imiquimod and ferulic acid. The IR Spectras of Imiquimod and cocrystals (Vertex 70, Bruker, Ettlingen, Germany; equipped with a globar mid-IR source) were obtained using an attenuated total reflectance (ATR) accessory (single reflection germanium crystal) and a DLaTGS detector. The resolution was 4 cm$^{-1}$, and 64 scans were acquired in the range of 4000-400 cm$^{-1}$. The peak positions were determined using OPUS software peak picking function.

FTIR, which can be used for the simultaneous study of the spectra of the cocrystals' individual components and of their final mixture with polymer matrices, etc., is an important tool in detecting cocrystal formation and in the elucidation of their structures. The cocrystal provides a different spectrum from that of the components' mixture due to the presence of hydrogen bonds, especially when a carboxylic acid is used as a coformer and when a neutral hydrogen bond O—H _ _ _ N is formed between an acid and a base. Clear IR spectra differences are observed between a neutral carboxylic acid functional group and a carboxylic anion. Neutral carboxylate (—COOH) shows a strong tension band of C=O at about 1700 cm).

The following samples were analyzed by FTIR:

TABLE 1

| Sample No. | Sample Name | Description |
|---|---|---|
| 1 | Imiquimod | |
| 2 | Ferulic acid | |
| 3 | IMQ-Fe | 20 mg IMQ + 16 mg Fe in 50 ml ethanol, the materials dissolved and ethanol was allowed to evaporate at RT |
| 4 | IMQ + Fe-ethanol trituration | 40 mg IMQ + 82 mg Fe + 20 mg ethanol, the dispersion was triturated (grinding) and ethanol was allowed to evaporate while triturating |

Figure 5:
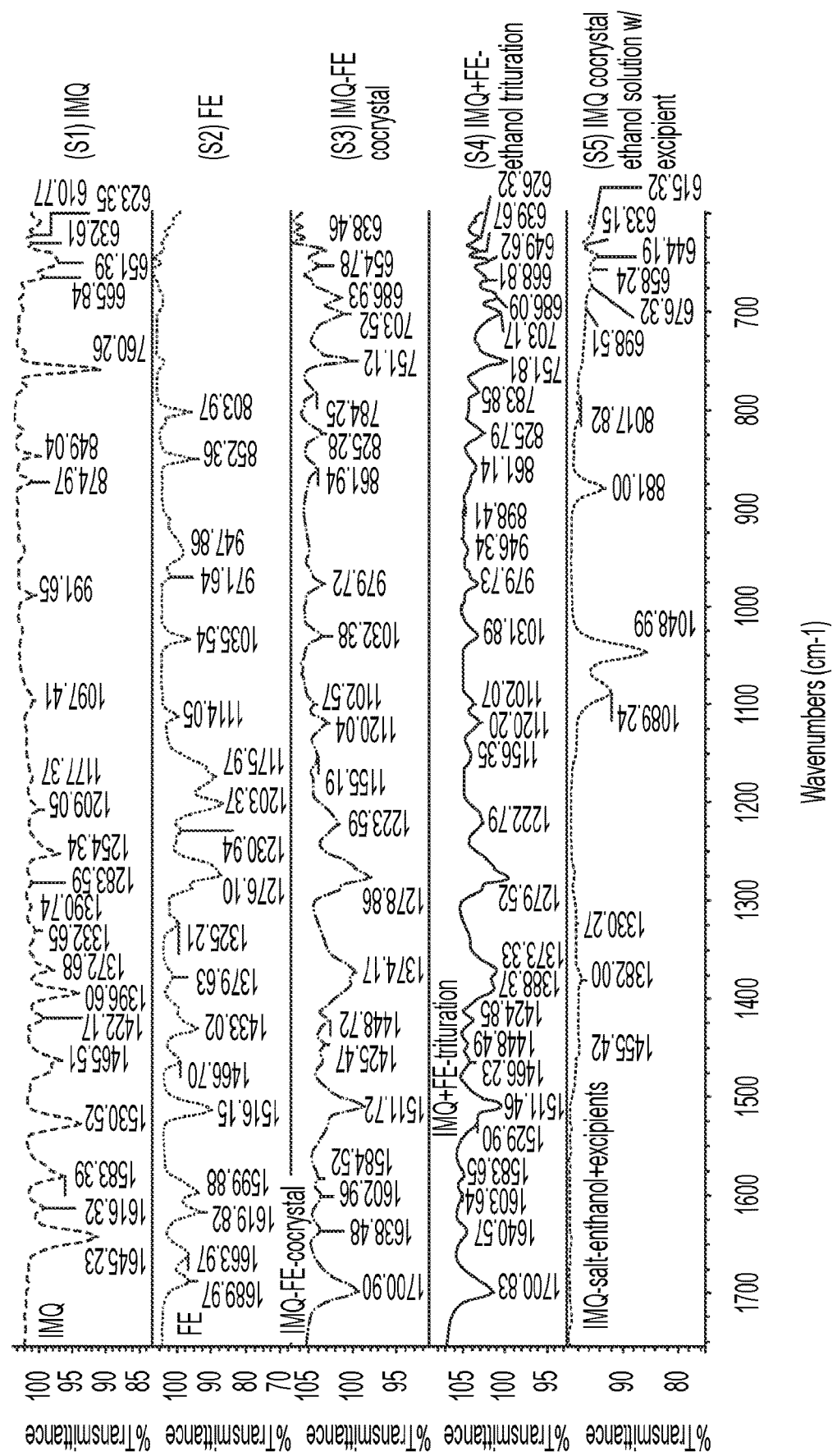
FIG. 5 provides a comparison of the FT-IR spectra of imiquimod, ferulic acid, IMQ-Fe, IMQ-Fe made by ethanol trituration, and to IMQ-Fe made in an ethanol solution with an excipient, over the wavelength range of 1700-600 $cm^{-1}$.

FIG. 5 shows a comparison of IR spectra for Samples 1-4 over the wavelength range of 1700-600 cm$^{-1}$.

Figure 6:
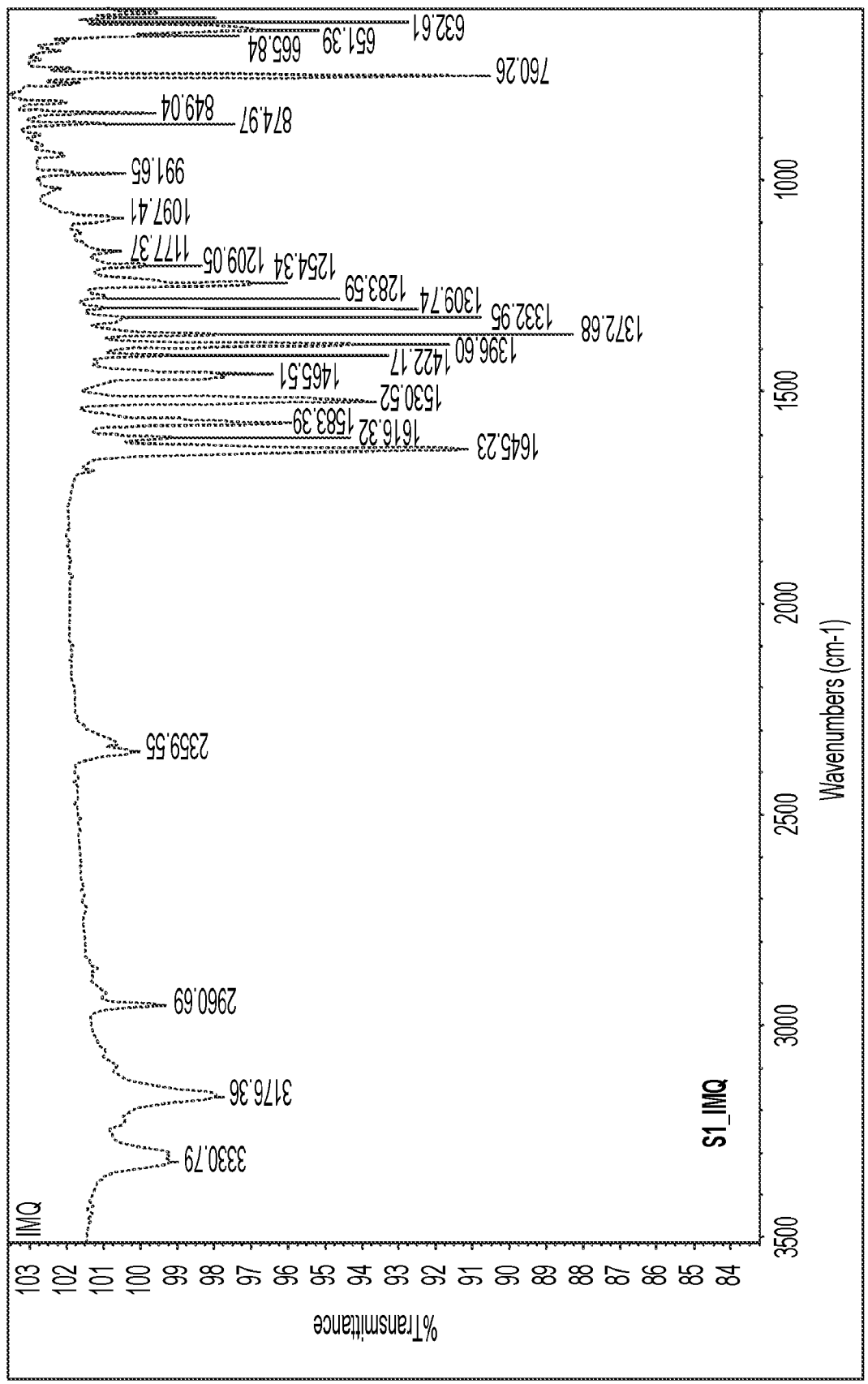
FIG. 6 is an IR spectrum of imiquimod, over the wavelength range of 3400-600 $cm^{-1}$.

FIG. 6 is an IR spectrum of imiquimod, over the wavelength range of 3400-600 cm$^{-1}$.

Figure 7:
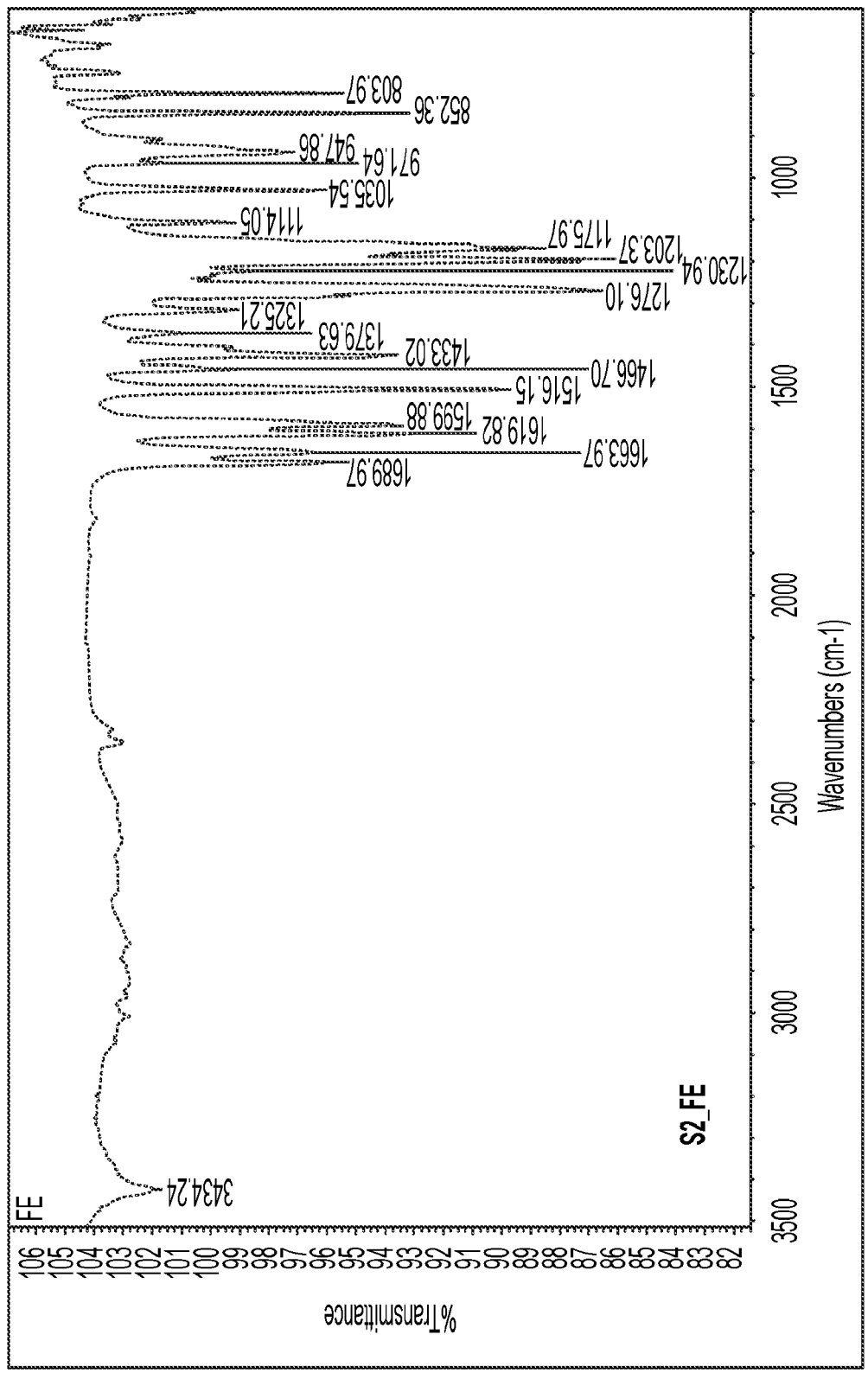
FIG. 7 is an IR spectrum of ferulic acid, over the wavelength range of 3400-600 $cm^{-1}$.

FIG. 7 is an IR spectrum of ferulic acid, over the wavelength range of 3400-600 cm$^{-1}$.

Figure 8:
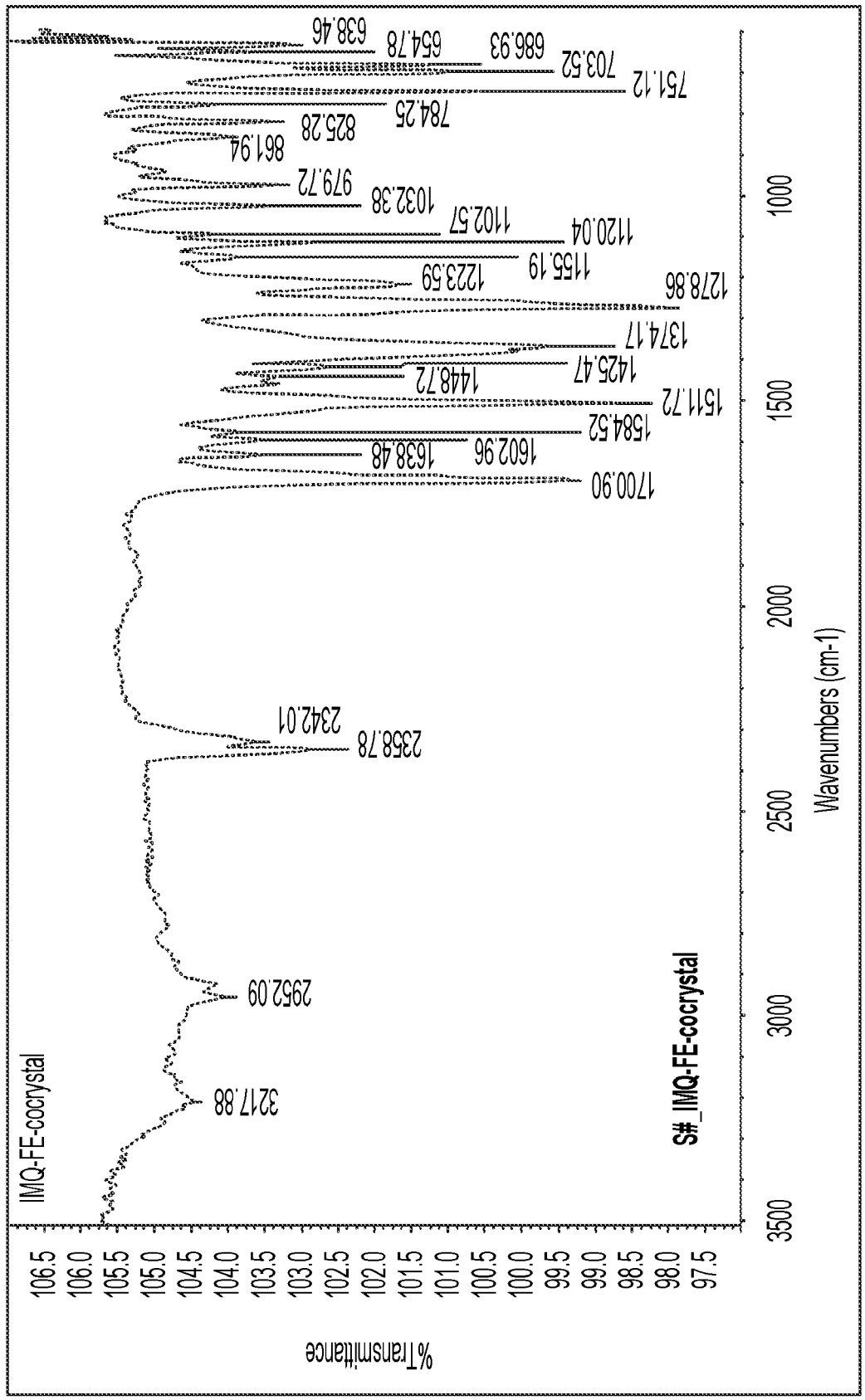
FIG. 8 is an IR spectrum of IMQ-Fe, over the wavelength range of 3400-600 $cm^{-1}$.

FIG. 8 is an IR spectrum of IMQ-Fe, over the wavelength range of 3400-600 cm$^{-1}$.

Figure 9:
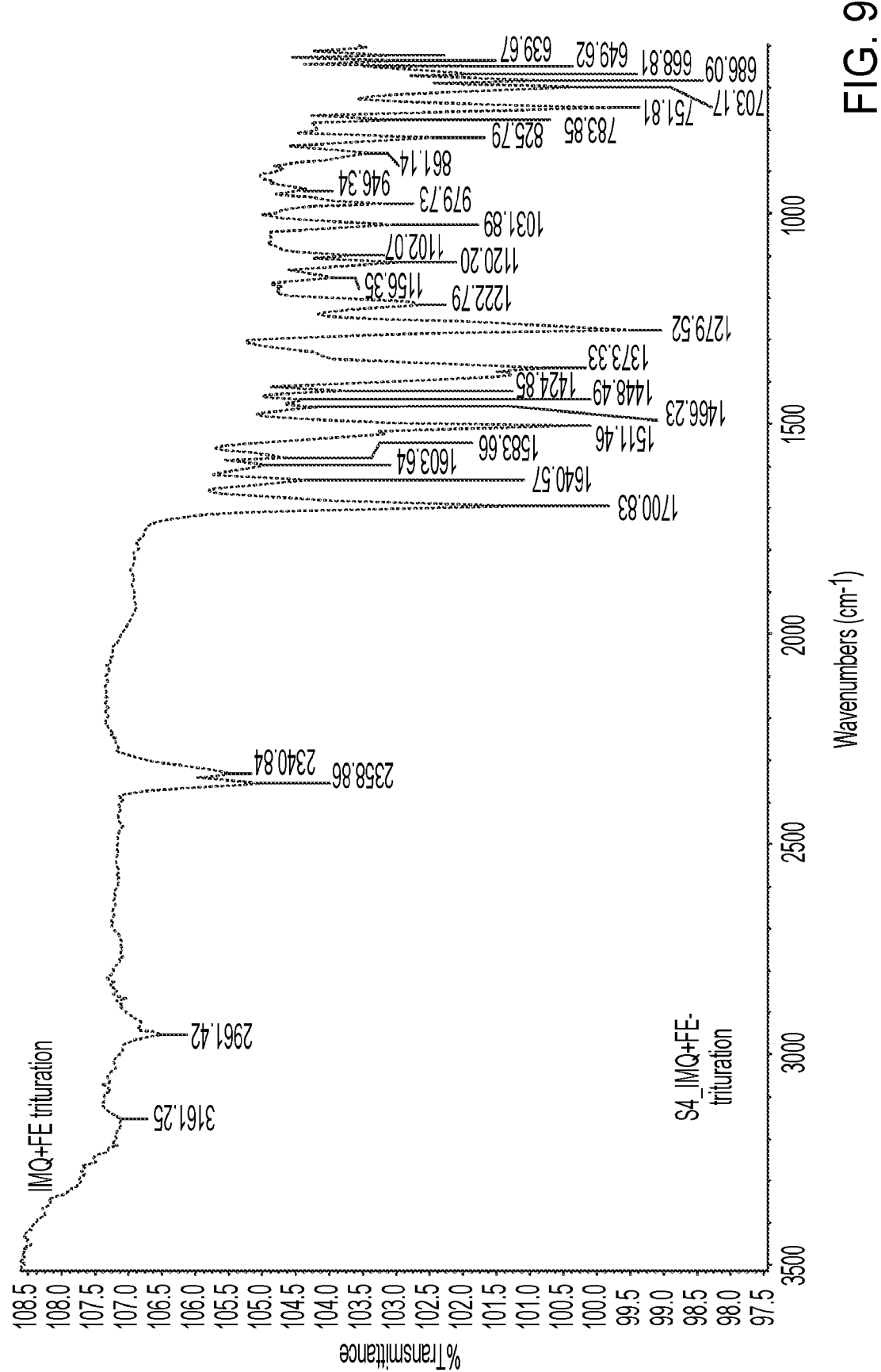
FIG. 9 is an IR spectrum of IMQ-Fe made by ethanol trituration, over the wavelength range of 3400-600 $cm^{-1}$.

FIG. 9 is an IR spectrum of IMQ-Fe-ethanol trituration, over the wavelength range of 3400-600 cm$^{-1}$.

If a salt forms, the wavenumbers of carboxylic acid groups at 1689 and 1663 cm$^{-1}$ (free and cyclic carboxylic acid, respectively) should decrease to the lower region around 1580-1620 cm$^{-1}$. However, for the imiquimod-ferulic acid complex, instead of decreasing, the new peak of carboxylic acid shifted to higher wavenumbers around 1700.90 cm$^{-1}$. This indicates that a cocrystal was formed rather than a salt. With regard to the samples for ethanol trituration, and ethanol solution with excipient, the peaks for ethanol and excipients may cover the characteristic peaks of imiquimod and ferulic acid when dissolved.

The IR data for samples 3 and 4 indicates that either method of preparation produces the same cocrystal. However, the morphology of the two samples appears to be different

Example 4 (IMQ-Ac)

IMQ-Ac was prepared by weighing equimolar amounts of imiquimod and acetic acid (0.2 mg imiquimod and 60.5 mg acetic acid) in 10 ml methanol, and then mixing and mechanically grinding them with mortar and pestle for up to 30 minutes at room temperature, 19-22° C. Small quantities of methanol were added at regular intervals of time. The total amount of methanol used was 10 ml. The solids (imiquimod and coformer) partially dissolved during grinding, such that they formed a wet powder or paste. During grinding most of the methanol evaporated. The mixture was dried in a vacuum oven at room temperature.

Samples of this imiquimod-acetic acid complex were evaluated using PXRD, TGA, and DSC, according to the protocols described in Example 2.

Figure 10:
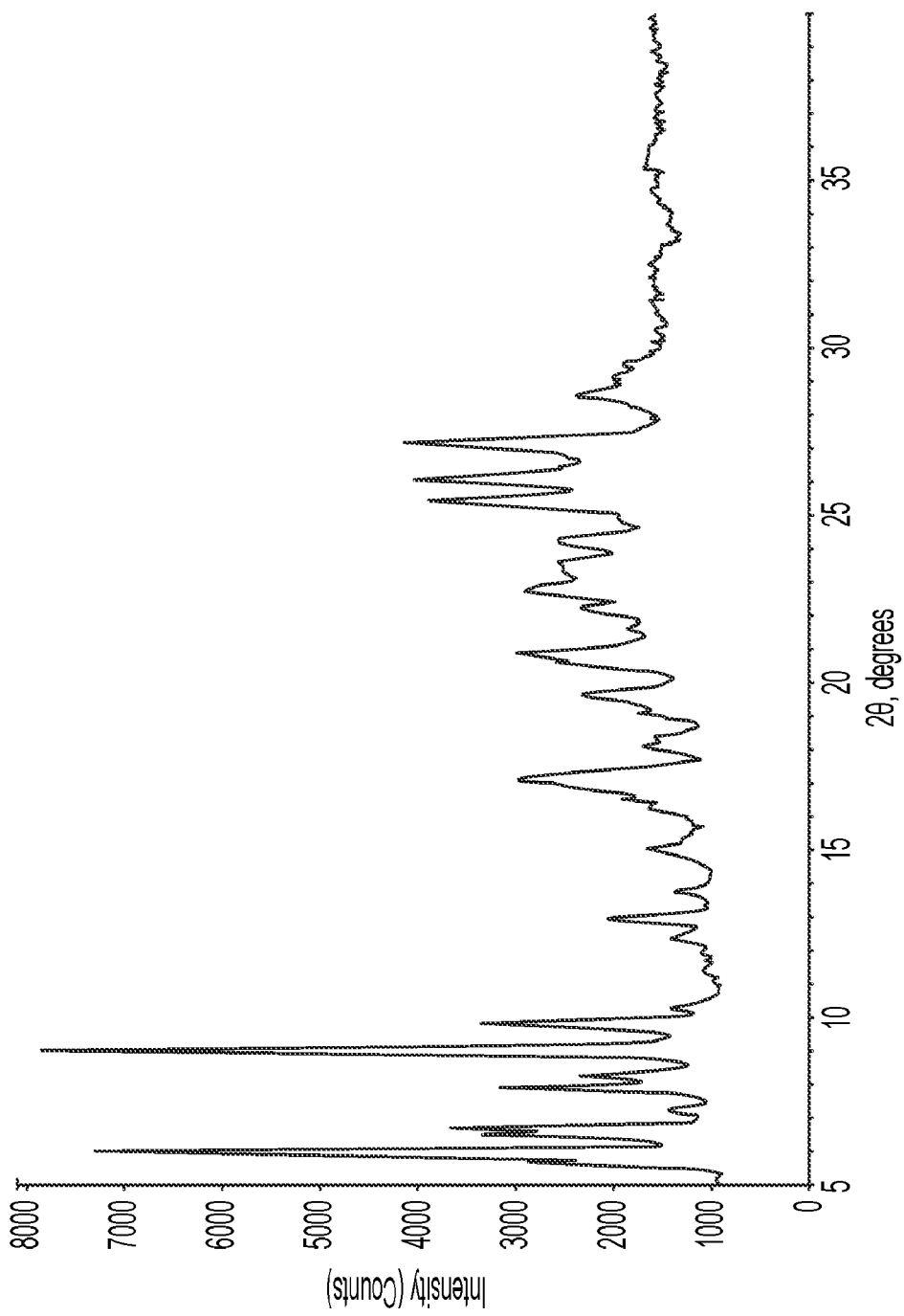
FIG. 10 is the PXRD pattern of the Imiquimod-acetic acid cocrystal IMQ-Ac.

The PXRD pattern of the complex is shown in FIG. 10. The pattern shows characteristic peaks with 2θ values at: 5.9, 6.7, 7.9, 9.0, 9.8, 12.9, 17.1, 20.8, 22.7, 25.5, 26.1 and 27.1°. Crystalline imiquimod has characteristic peaks with 2θ values of 11, 15, 19, 22 and 24°. [Reference: patent CA2551616A1]. Crystalline acetic acid has characteristic peaks with 2θ values of 110, 200, 210, and 311°. The PXRD pattern shown in FIG. 10 has characteristic peaks that appear only in the imiquimod-acetic acid complex, and are not found in the PXRD patterns for imiquimod or acetic acid. The appearance and disappearance of new peaks in the PXRD pattern of the complex, compared to the patterns for the individual components imiquimod and acetic acid, confirms a change in the crystalline structure and indicate the formation of a new cocrystal. Moreover, the PXRD pattern in FIG. 10 demonstrates that the complex was crystalline.

Figure 11:
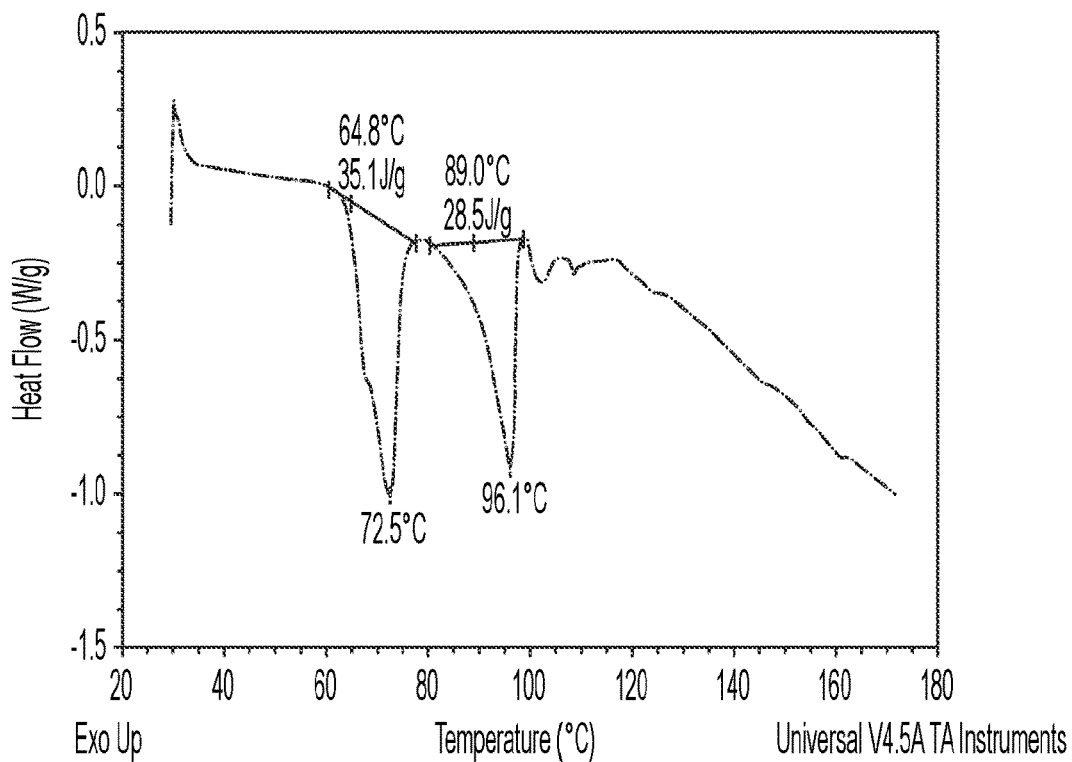
FIG. 11 is the DSC thermogram of the Imiquimod-acetic acid cocrystal IMQ-Ac.

DSC was used to evaluate the thermal behavior of a sample of the imiquimod-acetic acid complex. The DSC thermogram is shown in FIG. 11. The material has complex endotherms at about 64.8-72.5° C. and about 89.0-96.1° C. These temperatures fall between the melting point of imiquimod, which has a melting point of 292-296° C., and the melting point of acetic acid, which has a melting point of 16.6° C. This is strong evidence that a cocrystal is formed.

Figure 12:
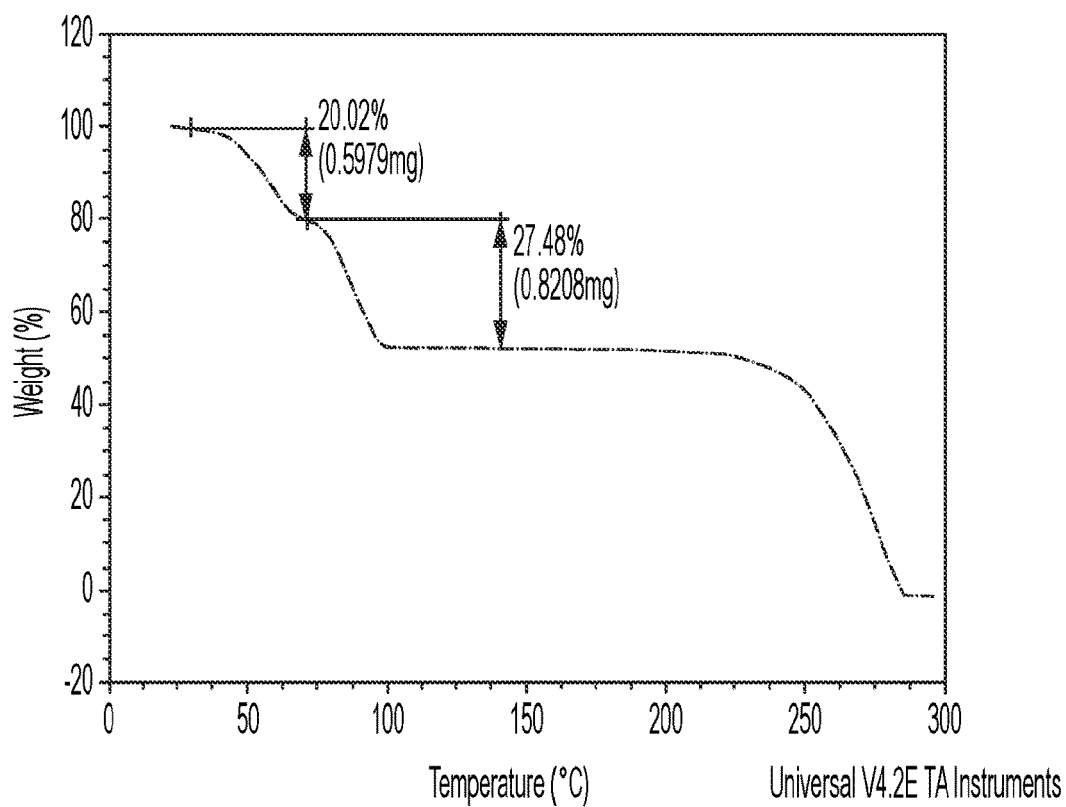
FIG. 12 is the TGA curve of the Imiquimod-acetic acid cocrystal IMQ-Ac.

TGA was used to evaluate the thermal stability of the complex. As shown in FIG. 12, two endotherms around the complex melting point appeared. The first endotherm may be a desolvation/dehydration event, which means that this cocrystal could be a hydrate or methanol solvate cocrystal.

The data generated by PXRD, DSC and TGA confirms that the newly formed imiquimod-acetic acid complex is a cocrystal. We have designated this new molecular complex IMQ-Ac.

Example 5 (IMQ-Co)

IMQ-Co was prepared by weighing equimolar amounts of imiquimod and coumaric acid (40 mg of imiquimod and 27 mg of coumaric acid) and then mixing and mechanically grinding them with mortar and pestle for 30 minutes, at room temperature, 19-22° C. Small quantities of methanol were added at regular intervals of time. The total amount of methanol used was 10 ml. The solids (imiquimod and coformer) partially dissolved during grinding, such that they formed a wet powder or paste. During grinding most of the methanol evaporated. The mixture was dried in a vacuum oven at room temperature.

Samples of this imiquimod-coumaric acid complex were evaluated using PXRD, TGA, and DSC, according to the protocols described in Example 2.

Figure 13:
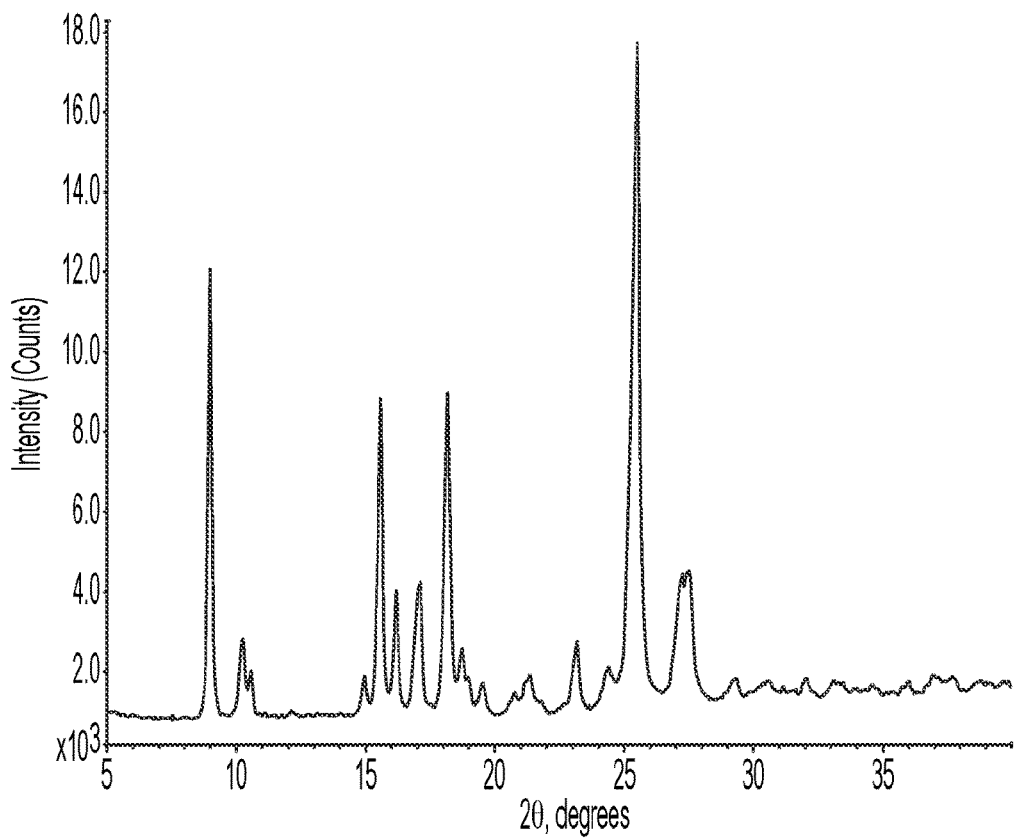
FIG. 13 is the PXRD pattern of the Imiquimod-coumaric acid cocrystal IMQ-Co.

The PXRD pattern of the complex is shown in FIG. 13. The pattern shows characteristic peaks with 2θ values at: 9.0, 10.2, 15.6, 16.2, 18.2, 23.2, 25.5 and 27.5°. Crystalline imiquimod has characteristic peaks with 2θ values of 11, 15, 19, 22 and 24°. [Reference: patent CA2551616A1]. Crystalline coumaric acid has characteristic peaks with 2θ values of 17.5, 19.8, 25.0, and 30.5°. The PXRD pattern shown in FIG. 13 has characteristic peaks that appear only in the imiquimod-coumaric acid complex, and are not found in the PXRD patterns for imiquimod or coumaric acid. The appearance and disappearance of new peaks in the PXRD pattern in this complex compared to the patterns for the individual components imiquimod and coumaric acid, confirms a change in the crystalline structure and indicate the formation of a new cocrystal. Moreover, the PXRD pattern in FIG. 13 demonstrates that the sample was crystalline.

Figure 14:
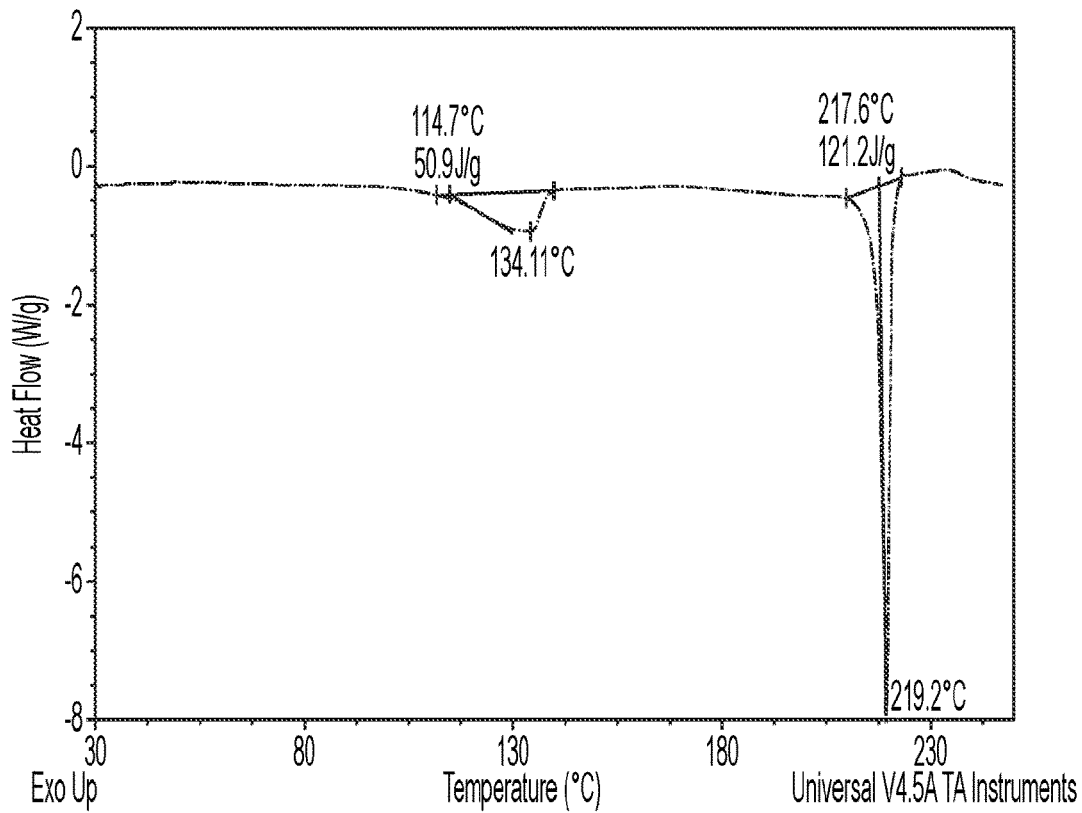
FIG. 14 is the DSC thermogram of the Imiquimod-coumaric acid cocrystal IMQ-Co.

DSC was used to evaluate the thermal behavior of the imiquimod-coumaric acid complex. The DSC thermogram is shown in FIG. 14. The material exhibited complex endotherms. It has two endotherms at about 114.7-134.11° C. and about 217.6-219.2° C. The first endotherm may be attributed to dehydration/desolvation and the second endotherm to the melting point, which suggests this could be a hydrate or methanol solvate cocrystal. The second endotherm falls between the melting point of imiquimod, which has a melting point of 292-296° C., and the melting point of p-coumaric acid, which is 210-213° C.

Figure 15:
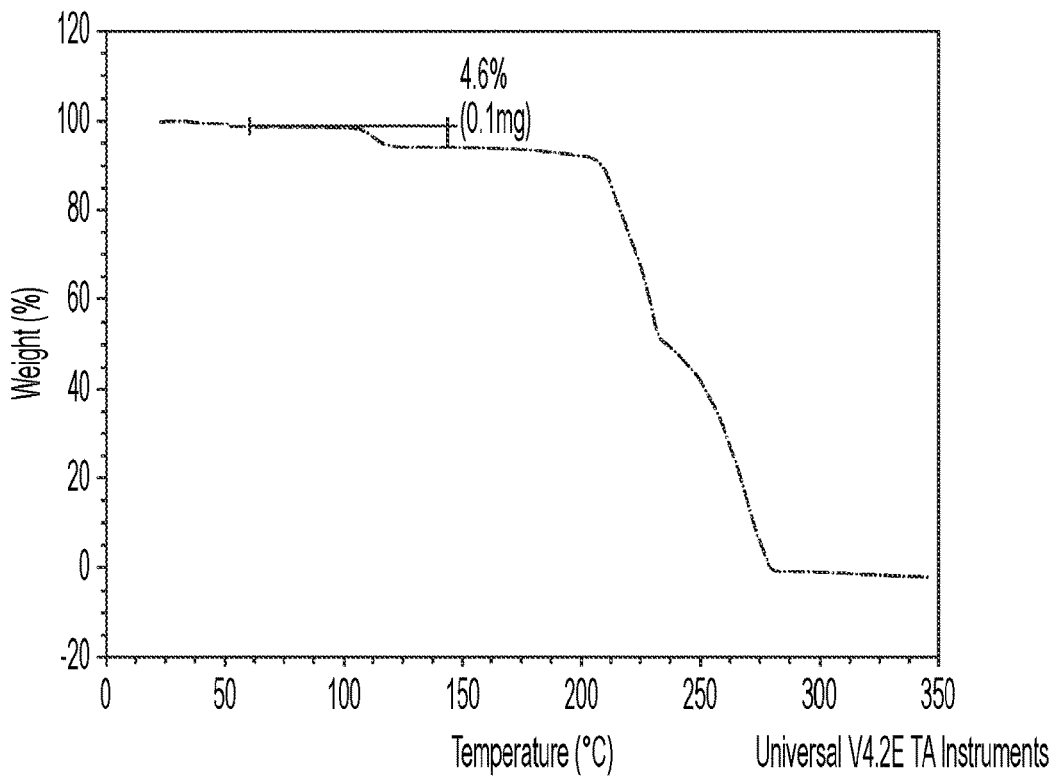
FIG. 15 is the TGA curve of the Imiquimod-coumaric acid cocrystal IMQ-Co.

TGA was used to evaluate the thermal stability of the sample. As shown in FIG. 15, an endotherm around the cocrystal melting point appeared. There was a 4.6% loss of water at about 150° C., indicating that this is a hydrate.

The data generated by PXRD, DSC and TGA confirms that the newly formed imiquimod-coumaric acid complex is a cocrystal. We have designated this new molecular complex IMQ-Co.

Example 6 (IMQ-Ci)

IMQ-Ci was prepared by weighing amounts of imiquimod and citric acid (80 mg of imiquimod and 32 mg of citric acid) to prepare a 2:1 molar mixture, and then mechanically grinding them with mortar and pestle for up to 30 minutes at room temperature, 19-22° C. Small quantities of methanol were added at regular intervals of time. The total amount of methanol used was 20 ml. The solids (imiquimod and coformer) partially dissolved during grinding, such that they formed a wet powder or paste. During grinding most of the methanol evaporated. The mixture was dried in a vacuum oven at room temperature.

Samples of this imiquimod-citric acid complex were evaluated using PXRD, TGA, and DSC, according to the protocols described in Example 2.

Figure 16:
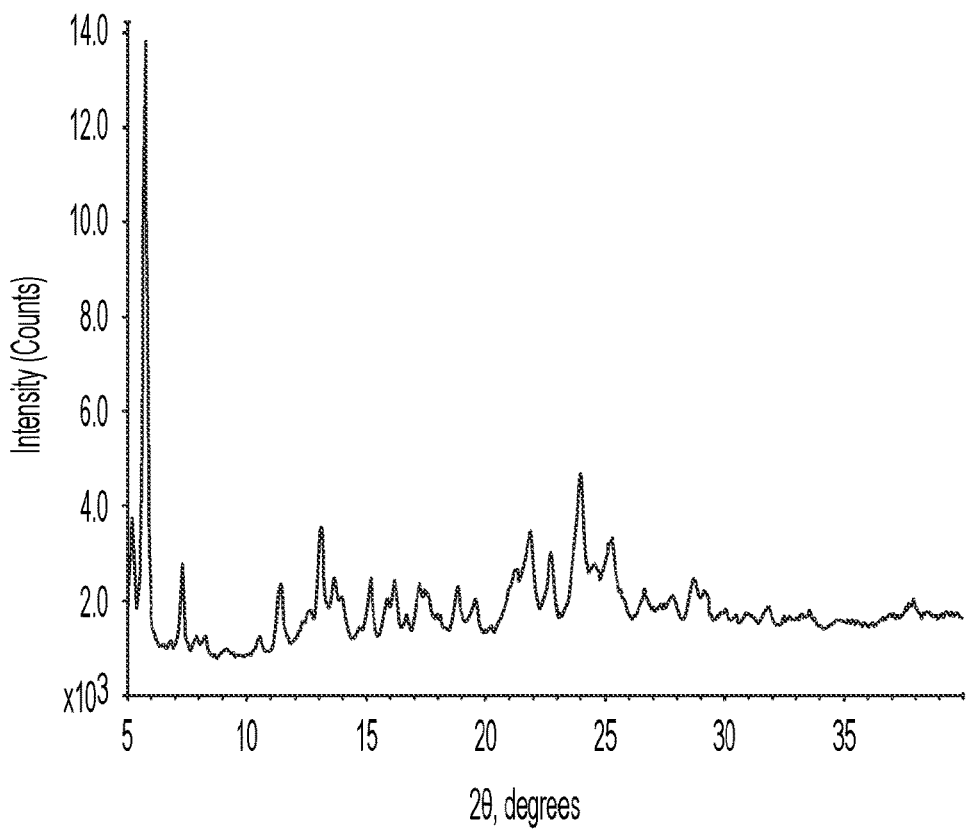
FIG. 16 is the PXRD pattern of the Imiquimod-citric acid cocrystal IMQ-Ci.

The PXRD pattern of this complex is shown in FIG. 16. The pattern shows characteristic peaks with 2θ values at: 5.2, 5.8, 7.3, 13.1, 13.7, 15.2, 21.9, 22.7, 23.4 and 25.3°. Crystalline imiquimod has characteristic peaks with 2θ values of 11, 15, 19, 22 and 24°. [Reference: patent CA2551616A1]. Crystalline citric acid has characteristic peaks with 2θ values of 14, 17, 19, 24, 26, and 29°. The PXRD pattern shown in FIG. 16 has characteristic peaks that appear only in the imiquimod-citric acid complex, and are not found in the PXRD patterns for imiquimod or citric acid. The appearance and disappearance of new peaks in the PXRD pattern of the imiquimod-citric acid complex compared to the patterns for the individual components imiquimod and citric acid, confirms a change in the crystalline structure and indicate the formation of a new cocrystal. Moreover, the PXRD pattern in FIG. 16 demonstrates that the sample was crystalline.

Figure 17:
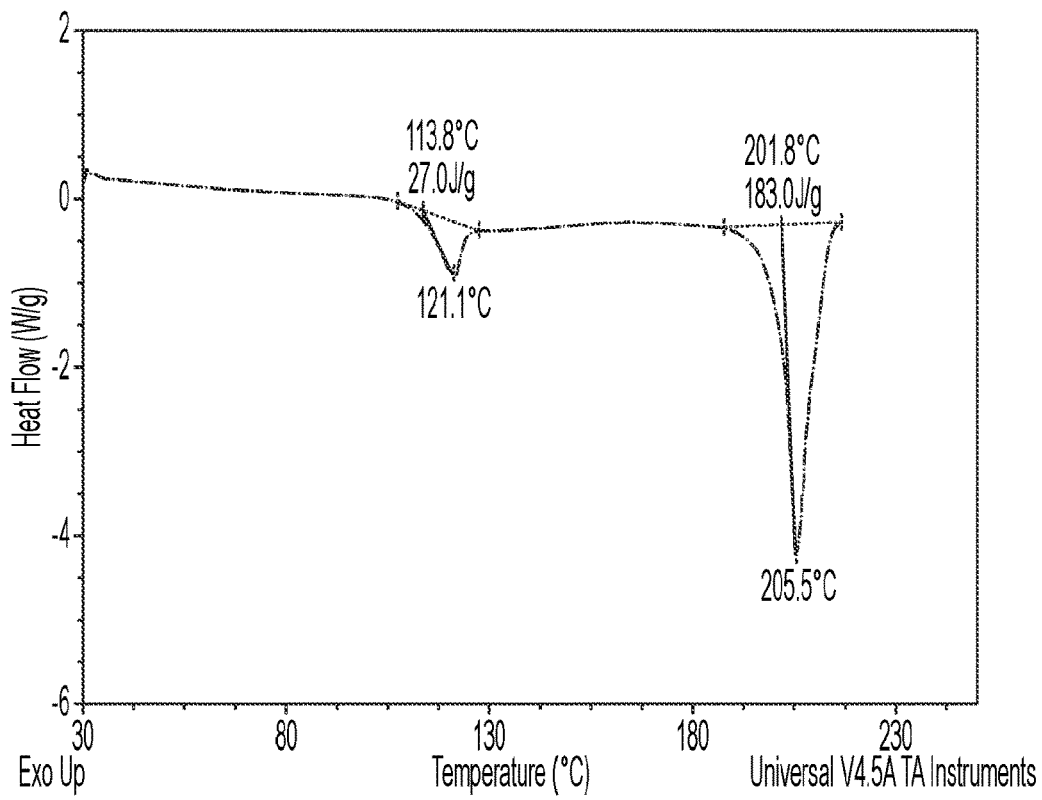
FIG. 17 is the DSC thermogram of the Imiquimod-citric acid cocrystal IMQ-Ci.

DSC was used to evaluate the thermal behavior of the imiquimod-citric acid complex. The DSC thermogram is shown in FIG. 17. The material has two endotherms at 113.8-121.1° C. and 201.8-205.5° C. The second endotherm falls between the melting point of imiquimod, which has a melting point of 292-296° C., and the melting point of citric acid, which has a melting point of 153° C. This is strong evidence that a cocrystal is formed.

Figure 18:
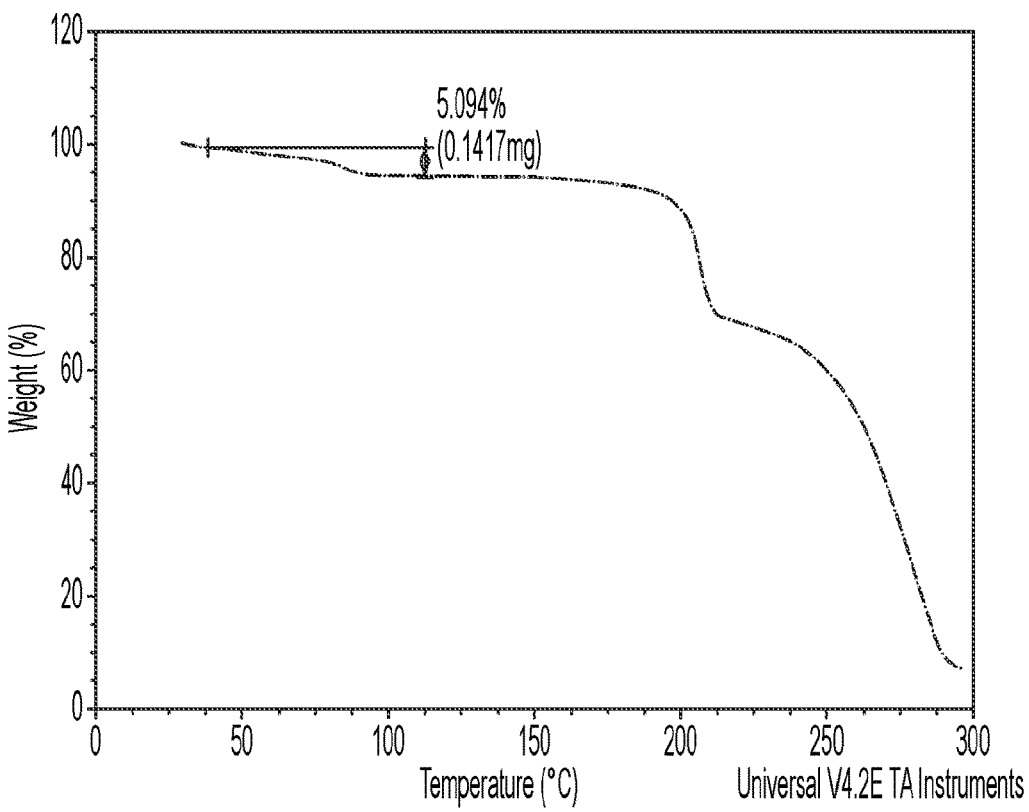
FIG. 18 is the TGA curve of the Imiquimod-citric acid cocrystal IMQ-Ci.

TGA was used to evaluate the thermal stability of the complex. As shown in FIG. 18, two endotherms which were lower than those of citric acid and imiquimod respectively appeared. The curve also indicates the crystal is stable at least up to 180° C.

The first endotherm may be a desolvation/dehydration event, which means that this cocrystal could be a hydrate or methanol solvate cocrystal. There was a 5.0% weight loss at about 120° C., indicating this is a hydrate.

The data generated by PXRD, DSC and TGA confirms that the newly formed imiquimod-citric acid complex is a cocrystal. We have designated this new molecular complex IMQ-Ci.

Example 7 (IMQ-Tar)

IMQ-Tar was prepared by weighing amounts of imiquimod and tartaric acid (80 mg of imiquimod and 25 mg of tartaric acid) to prepare a 2:1 molar mixture, and then mechanically grinding the mixture with mortar and pestle for up to 30 minutes at room temperature, 19-22° C. Small quantities of methanol were added at regular intervals of time. The total amount of methanol used was 20 ml. The solids (imiquimod and coformer) partially dissolved during grinding, such that they formed a wet powder or paste. During grinding most of the methanol evaporated. The mixture was dried in a vacuum oven at room temperature.

Samples of this imiquimod-tartaric acid complex were evaluated using PXRD, TGA, and DSC, according to the protocols described in Example 2.

Figure 19:
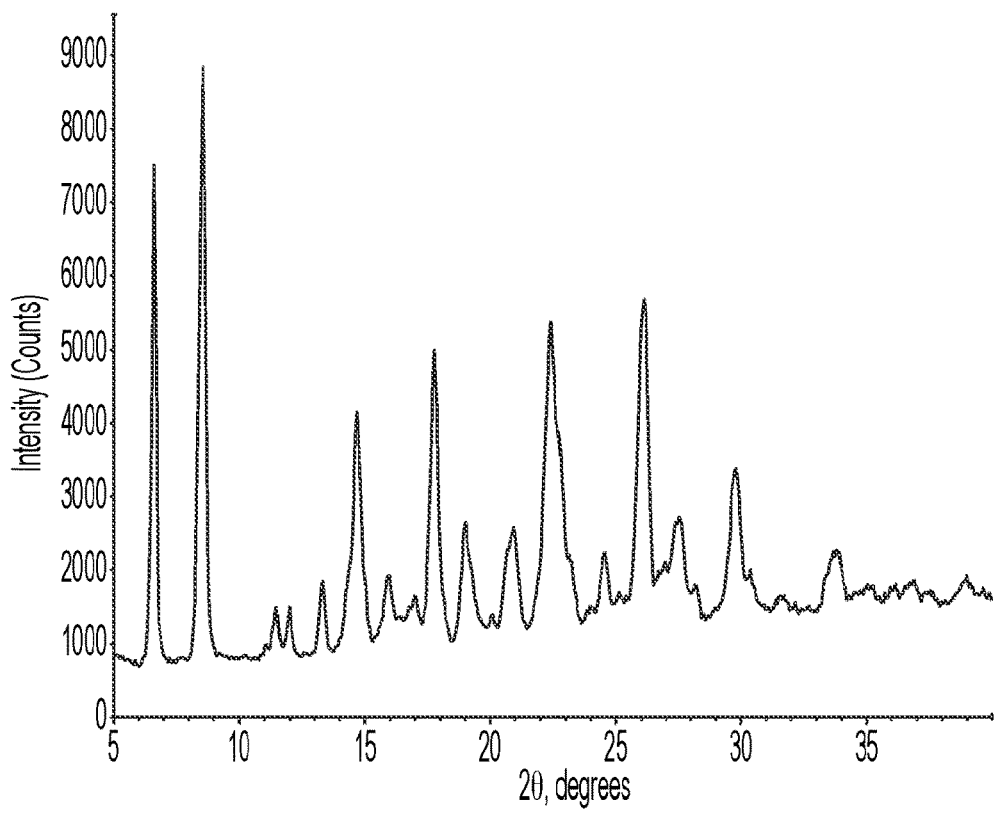
FIG. 19 is the PXRD pattern of the Imiquimod-tartaric acid cocrystal IMQ-Tar.

The PXRD pattern this complex is shown in FIG. 19. The pattern shows characteristic peaks with 2θ values at: 6.6, 8.5, 13.3, 14.7, 17.8, 19.0, 20.9, 22.4, 26.1, 27.5 and 29.8°. Crystalline imiquimod has characteristic peaks with 2θ values of 11, 15, 19, 22 and 24°. [Reference: patent CA2551616A1]. Crystalline tartaric acid has characteristic peaks with 2θ values of 11.5, 20.5, 25, 29 and 36°. The PXRD pattern shown in FIG. 19 has characteristic peaks that appear only in the imiquimod-tartaric acid complex, and are not found in the PXRD patterns for imiquimod or tartaric acid. The appearance and disappearance of new peaks in the PXRD pattern for the complex, compared to the patterns for the individual components, imiquimod and tartaric acid, confirms a change in the crystalline structure and indicate the formation of a new cocrystal. Moreover, the PXRD pattern in FIG. 19 demonstrates that the sample was crystalline DSC was used to evaluate the thermal behavior of the imiquimod-tartaric acid complex. No melting point or endotherm was detected.

Figure 20:
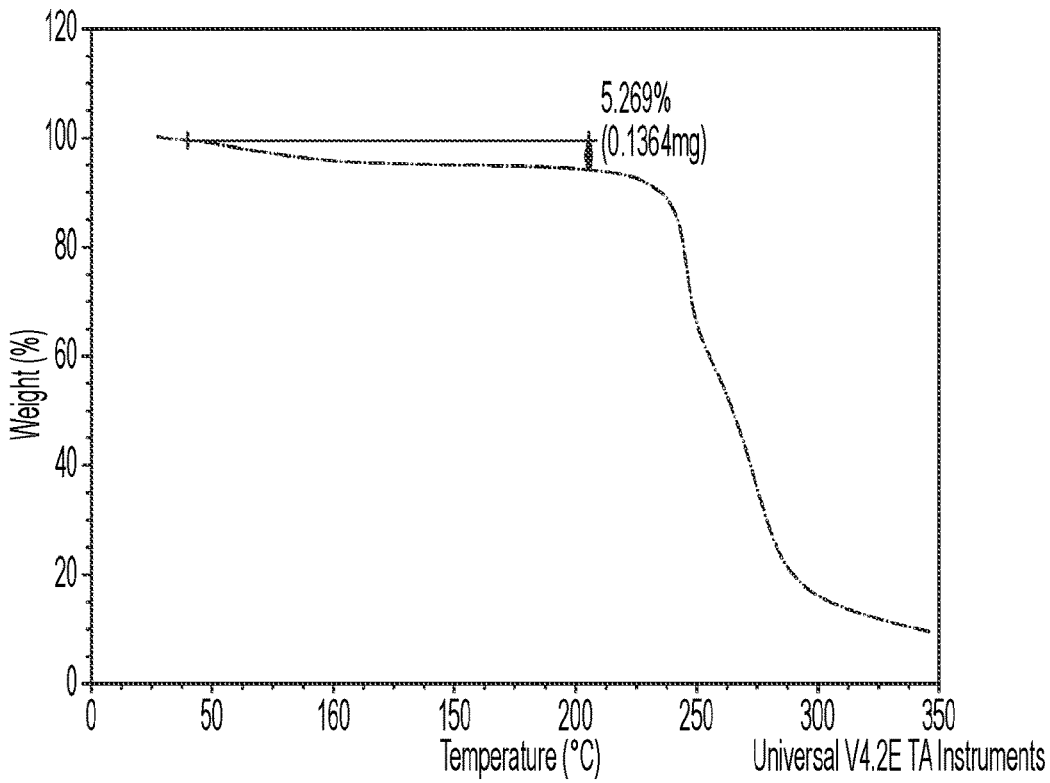
FIG. 20 is the TGA curve of the Imiquimod-tartaric acid cocrystal IMQ-Tar.

TGA was used to evaluate the thermal stability of the sample. As shown in FIG. 20, one endotherm appeared. This endotherm may be a desolvation/dehydration event, which means that this cocrystal could be a hydrate or methanol solvate cocrystal. The curve also indicates the crystal is stable until around 220° C. There was a 5.2% loss of water at about 170° C., indicating that this is a hydrate.

The data generated by PXRD, DSC and TGA confirms that the newly formed imiquimod-tartaric acid complex is a cocrystal. We have designated this new molecular complex IMQ-Tar.

Example 8-Solubility of Imiquimod and Imiquimod-Ferulic Acid Co-Crystal

Figure 21:
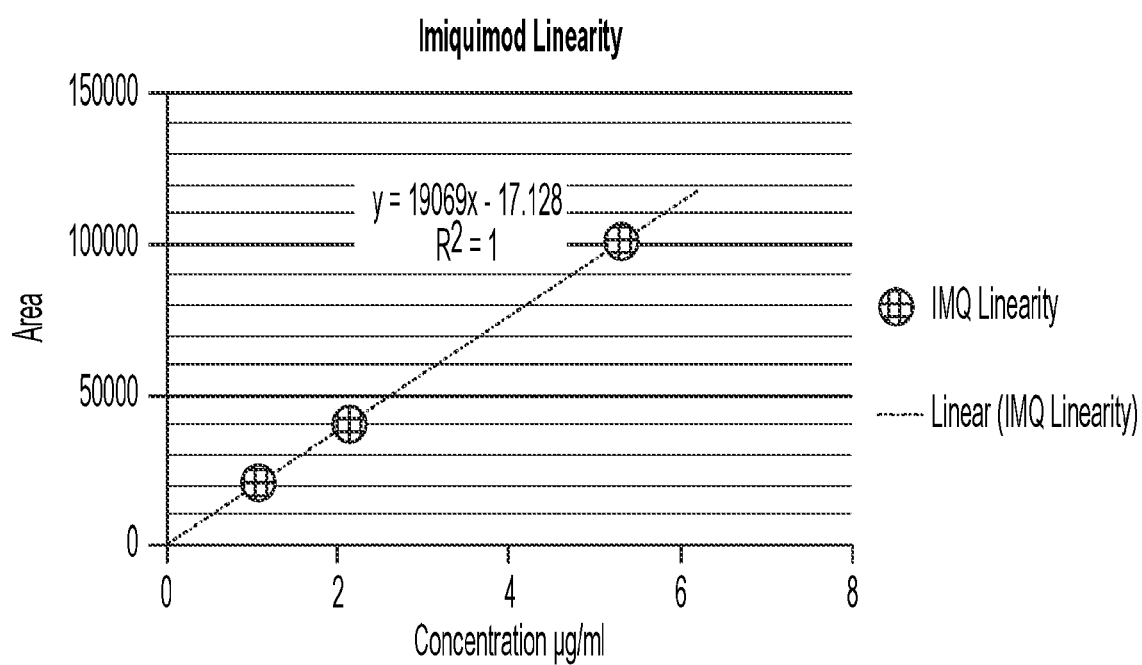
FIG. 21 depicts the Calibration Curve for Imiquimod.

The solubility of imiquimod and the imiquimod-ferulic acid cocrystal in water was evaluated. Each sample (Imiquimod, IMQ-Fe, or Ferulic Acid) was dissolved in water. Imiquimod was assayed using a reverse phase chromatographic method utilizing a Waters UPLC. The amount of imiquimod in samples of aqueous solutions of imiquimod was assayed by comparing to external standards. In the same sequence a ferulic acid standard was also run that allowed for independent calculation of ferulic acid content in cocrystal samples. The calibration curve for Imiquimod is shown in FIG. 21.

TABLE 2

Aqueous Solubility of Imiquimod, Ferulic Acid and IMQ-Fe

| Sample in water | Calculated Sample Concentration (mg/ml) | Calculated Sample Concentration (µg/ml) | Comment |
|---|---|---|---|
| Imiquimod | 0.0022 | 2.2 | Imiquimod |
| IMQ-Fe | IMQ 0.0939 | 93.9 | Imiquimod |
|  | FA 0.1141 | 114.1 | Ferulic acid |
| Ferulic Acid | 0.8155 | 815.5 | Ferulic acid |

In addition to solubility, the pH of Imiquimod and IMQ-Fe were evaluated using a pH probe. The results are shown in the table below. The pH of Imiquimod was found to be 7.10 and the pH of IMQ-Fe was found to be 5.64.

TABLE 3

Aqueous Solubility of Imiquimod/Ferulic Acid Cocrystal

| Sample | Component | Concentration (unheated, mg/ml) | Concentration (heated for 1 hr @ 60 C., mg/ml) | pH |
|---|---|---|---|---|
| Imiquimod | IMQ | 0.002 | 0.002 | 7.10 |
| IMQ-Fe | IMQ | 0.049 (40.4%) | 0.094 (44.3%) | 5.64 |

Imiquimod is practically insoluble in water and sparingly soluble in other common organic solvents. The IMQ-Fe Cocrystal of the invention has significantly improved solubility, compared to imiquimod. The IMQ-Fe sample at equilibrium maximum aqueous solubility conditions demonstrates an enhanced solubility of approximately 40 times compared to the imiquimod sample.

In addition, the cocrystal IMQ-Fe was found to be stable at 40° C. 75% RH for at least a week.

Example 9: Summary of Cocrystal Evaluation

TABLE 4

| Cocrystal | PXRD (Novel Phase) | DSC | TGA | Comments |
|---|---|---|---|---|
| IMQ-Ci | ✓ 5.8, 23.4 | Unique melting point 121.1 &205.5 | 5.0% weight loss at 120° C. | Appears to be a hydrate |
| IMQ-Ac | ✓ 6.7, 9.0 | Complex endotherms 72.5 & 96.1 | Two weight losses observed | Complex system |
| IMQ-Tar | ✓ 8.5, 26.1 | No melting peak observed up to 200 ° C. | 5.2% weight loss at 170° C. | Appears to be a hydrate |
| IMQ-Fe | ✓ 13.3, 28.1 | Unique melting point 226.4 | Negligible weight loss (~1%) up to 180 ° C.) | Appears to be anhydrous |
| IMQ-Co | ✓ 9.0, 25.5 | Unique melting point 134.1 & 219.2 | 4.6% water at 150° C. | Appears to be a hydrate |

Although the present invention herein has been described with reference to various exemplary embodiments, it is to be understood that these embodiments are merely illustrative of the principles and applications of the present invention. Those having skill in the art would recognize that a variety of modifications to the exemplary embodiments may be made, without departing from the scope of the invention.

Moreover, it should be understood that various features and/or characteristics of differing embodiments herein may be combined with one another. It is therefore to be understood that numerous modifications may be made to the illustrative embodiments and that other arrangements may be devised without departing from the scope of the invention.

The invention claimed is:

1. A molecular complex of imiquimod and ferulic acid, which is IMQ-FA.

2. The molecular complex of claim 1, wherein the molar ratio of imiquimod to ferulic acid is from 0.8:1.0 to 1.0:0.8.

3. The molecular complex of claim 1, wherein the ratio of imiquimod to ferulic acid is equimolar.

4. The molecular complex of claim 1, wherein the molecular complex has a PXRD pattern, using Cu-Kα radiation, expressed as 2θ angles, with at least two peaks at positions selected from the following group: 12.3±0.2°, 13.3±0.2°, 15.1±0.2°, 17.2±0.2°, 17.7±0.2°, 17.9±0.2°, 18.7±0.2°, 19.5±0.2°, 19.9±0.2°, 23.5±0.2°, 24.7±0.2°, 25.7±0.2°, 26.9±0.2°, 27.5±0.2°, 28.1±0.2°, 28.9±0.2°, 29.5±0.2°, 30.4±0.2°, and 31.5±0.2°.

5. The molecular complex of claim 4, wherein the PXRD pattern has at least 4 peaks selected from the group.

6. The molecular complex of claim 1, wherein the molecular complex has a PXRD pattern, using Cu-Kα radiation, expressed as 2θ angles, with peaks at positions 13.3±0.2° and 28.1±0.2°.

7. The molecular complex of claim 1, wherein the IMQ-FA has a powder X-ray diffraction pattern substantially the same as that shown in FIG. 1.

8. The molecular complex of claim 1, wherein the molecular complex has an endotherm at 225-227° C.±3.0° C., as measured by differential scanning calorimetry (DSC).

9. The molecular complex of claim 1, wherein the molecular complex has an endotherm at 226.4±3.0° C., as measured by DSC.

10. The molecular complex of claim 1, wherein the molecular complex has an endotherm at 226.4° C., as measured by DSC.

11. The molecular complex of claim 1, wherein the molecular complex has less than 5% weight loss up to 180° C. as measured by thermogravimetric analysis (TGA).

12. The molecular complex of claim 1, wherein the molecular complex is anhydrous.

13. The molecular complex of claim 1, wherein the Fourier-transform infrared spectrum of the molecular complex has a carboxylic acid peak at 1700.90±5.0 cm$^{-1}$.

14. The molecular complex of claim 1, wherein the molecular complex was prepared by grinding equimolar amounts of imiquimod and ferulic acid in methanol.

15. The molecular complex of claim 1, wherein said molecular complex is substantially pure.

16. A method of making a molecular complex, comprising grinding imiquimod and ferulic acid in the presence of an organic solvent to obtain a molecular complex; wherein the molecular complex has an endotherm at about 225-227° C.±3.0° C. as measured by DSC, and/or a PXRD pattern using Cu-Kα radiation, expressed as 2θ angles, with peaks at positions 13.3±0.2° and 28.1±0.2°.

17. The method of claim 16, wherein the molar ratio of imiquimod to ferulic acid is from 0.8:1.0 to 1.0:0.8, and the grinding is performed at 15° C.-22° C.

18. The method of claim 16, wherein the imiquimod and ferulic acid are present in equimolar amounts and the grinding is performed at 15° C.-22° C.

19. A composition comprising the molecular complex of claim 1 and one or more pharmaceutically acceptable excipients.

* * * * *